(12) United States Patent
Rohler et al.

(10) Patent No.: US 6,292,783 B1
(45) Date of Patent: Sep. 18, 2001

(54) PHONE-ASSISTED CLINICAL DOCUMENT INFORMATION COMPUTER SYSTEM FOR USE IN HOME HEALTHCARE, POST-ACUTE CLINICAL CARE, HOSPICE AND HOME INFUSION APPLICATIONS

(75) Inventors: David P. Rohler, University Heights; Thomas E. Dechant, Chagrin Falls; Michelle F. Boasten, Akron, all of OH (US)

(73) Assignee: Plexar & Associates, Solon, OH (US)

( * ) Notice: Subject to any disclaimer, the term of this patent is extended or adjusted under 35 U.S.C. 154(b) by 0 days.

(21) Appl. No.: 09/036,179

(22) Filed: Mar. 6, 1998

(51) Int. Cl.[7] .................................................. G06F 17/00
(52) U.S. Cl. ........................................ 705/2; 705/3
(58) Field of Search ................................. 705/2, 3

(56) References Cited

U.S. PATENT DOCUMENTS

| | | | |
|---|---|---|---|
| 4,916,441 | * | 4/1990 | Gombrich ................................. 705/2 |
| 5,065,315 | * | 11/1991 | Garcia ..................................... 705/2 |
| 5,301,105 | * | 4/1994 | Cummings ................................ 705/2 |
| 5,361,202 | * | 11/1994 | Doue ...................................... 705/3 |
| 5,367,555 | * | 11/1994 | Isoyama .................................. 379/38 |
| 5,664,207 | * | 9/1997 | Crumpler et al. ........................ 705/3 |
| 5,724,580 | * | 3/1998 | Levin et al. ............................. 705/2 |
| 5,842,173 | * | 11/1998 | Strum et al. ............................. 705/1 |
| 5,845,253 | * | 12/1998 | Rensimer et al. ........................ 705/2 |
| 5,867,821 | * | 2/1999 | Ballantyne et al. ...................... 705/2 |

* cited by examiner

*Primary Examiner*—Allen R. MacDonald
*Assistant Examiner*—Forest Thompson, Jr.
(74) *Attorney, Agent, or Firm*—David J. Untener; Teresan W. Gilbert; Robert H. Earp III

(57) ABSTRACT

A document information system and a computer implemented method for use in the field of home healthcare, post-acute clinical care, hospice and home infusion comprising a data storage means, phone interface means for inputting and retrieving data and a verification means using one or more calendars to verify medical tasks.

17 Claims, 67 Drawing Sheets

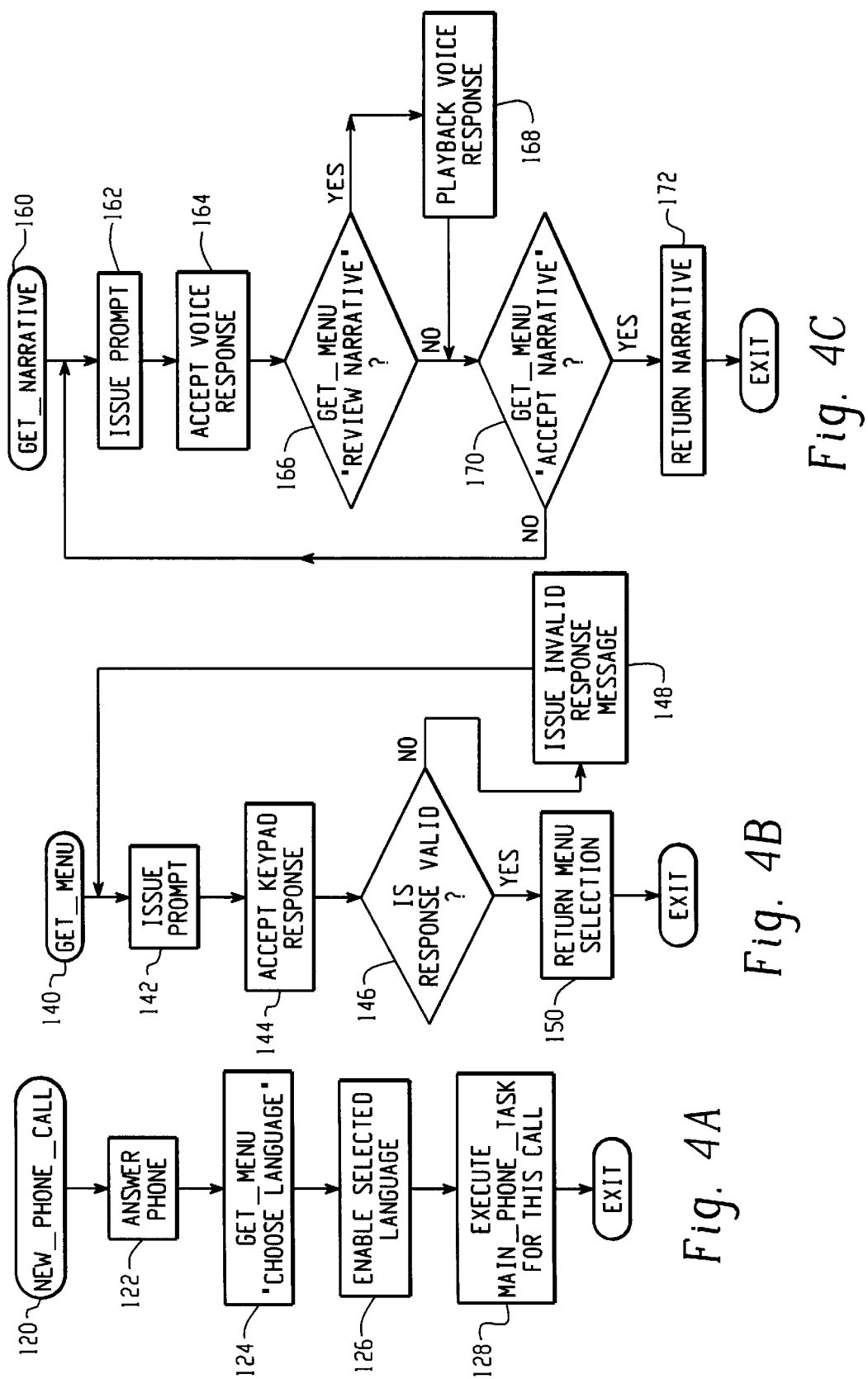

WHAT SHOULD OCCUR CALENDAR

| WEEK | Mon. | Tues. | Wed. | Thurs. | Fri. | Sat. | Sun. | TOTALS Visits, Hr |
|---|---|---|---|---|---|---|---|---|
| 1 | Feb 11, 97 | 2/12 RN HHA 9A-11A(2) | 2/13 RN HHA 9A-11A(2) | 2/14 HHA 9A-11A(2) | 2/15 RN HHA 9A-11A(2) SW | 2/16 | 2/17 | RN(3) HHA(4)(8) SW(1) |
| 2 | 2/18 RN HHA 9A-11A(2) | 2/19 HHA 9A-11A(2) | 2/20 RN HHA 9A-11A(2) | 2/21 HHA 9A-11A(2) | 2/22 RN HHA 9A-11A(2) | 2/23 | 2/24 | RN(3) HHA(5)(10) |
| 3 | 2/25 RN HHA 9A-11A(2) | 2/26 HHA 9A-11A(2) | 2/27 RN HHA 9A-11A(2) | 2/28 HHA 9A-11A(2) | March 1, 97 RN HHA 9A-11A(2) | 3/2 | 3/3 | RN(3) HHA(5)(10) |
| 4 | 3/4 RN | 3/5 HHA 9A-11A(2) | 3/6 RN | 3/7 HHA 9A-11A(2) | 3/8 RN | 3/9 HHA 9A-11A(2) | 3/10 | RN(3) HHA(5)(10) |
| 5 | 3/11 RN | 3/12 HHA 9A-11A(2) | 3/13 RN | 3/14 HHA 9A-11A(2) | 3/15 RN | 3/16 HHA 9A-11A(2) | 3/17 | RN(3) HHA(3)(6) |

Fig. 13A

WHAT ACTUALLY HAPPENED CALENDAR

| WEEK | Mon. | Tues. | Wed. | Thurs. | Fri. | Sat. | Sun. | TOTALS Visits,Hr |
|---|---|---|---|---|---|---|---|---|
| 1 | Feb 11,97 | 2/12 RN HHA 9:30A-11:30A (2) | 2/13 HHA 9A-11A(2) | 2/14 RN HHA 9A-11A(2) | 2/15 RN Sw | 2/16 HHA 9A-11A(2) | 2/17 | RN(3) HHA(4)(8) Sw(1) |
| 2 | 2/18 RN HHA 9A-11A(2) | 2/19 HHA 9A-11A(2) | 2/20 | 2/21 HHA 9A-11A(2) | 2/22 RN HHA 9A-11:30A (2.5) | 2/23 | 2/24 | RN(2) HHA(5)(10.5) |
| 3 | 2/25 RN HHA 9A-10A(1) | 2/26 HHA 9A-11A(2) | 2/27 RN HHA 9A-11A(2) | 2/28 HHA 9A-11A(2) | March 1,97 RN HHA 9A-11A(2) | 3/2 RN | 3/3 | RN(3) HHA(5)(9) |
| 4 | 3/4 RN | 3/5 HHA 9A-11A(2) | 3/6 | 3/7 RN HHA 9A-11A(2) | 3/8 | 3/9 | 3/10 | RN(2) HHA(2)(4) |

Fig. 13B

VERIFIER CALENDAR

| WEEK | Mon. | Tues. | Wed. | Thurs. | Fri. | Sat. | Sun. | PLAN Visits,Hr | DONE Visits,Hr |
|---|---|---|---|---|---|---|---|---|---|
| 1 | Feb 11,97 | 2/12 RN HHA 9A-11A(2) HHA 9:30A-11:30A (2) | 2/13 RN HHA 9A-11A(2) | 2/14 RN HHA 9A-11A(2) | 2/15 RN HHA 9A-11A(2) Sw | 2/16 HHA 9A-11A(2) | 2/17 | RN(3) HHA(4)(8) Sw(1) | RN(3) HHA(4)(8) Sw(1) |
| 2 | 2/18 RN HHA 9A-11A(2) | 2/19 HHA 9A-11A(2) | 2/20 RN HHA 9A-11A(2) | 2/21 HHA 9A-11A(2) | 2/22 RN HHA 9A-11A(2) HHA 9A-11:30A (2.5) | 2/23 | 2/24 | RN(3) HHA(5)(10) | RN(2) HHA(5)(10.5) |
| 3 | 2/25 RN HHA 9A-11A(2) HHA 9A-10A(1) | 2/26 RN HHA 9A-11A(2) | 2/27 RN | 2/28 | March 1,97 RN HHA 9A-11A(2) | 3/2 RN | 3/3 | RN(3) HHA(5)(10) | RN(3) HHA(5)(9) |
| 4 | 3/4 RN | 3/5 HHA 9A-11A(2) | 3/6 RN | 3/7 RN HHA 9A-11A(2) | 3/8 RN | 3/9 HHA 9A-11A(2) | 3/10 | RN(3) HHA(3)(6) | RN(2) HHA(2)(4) |

Fig. 13C

ULTIMATE AUDITOR CALENDAR

| WEEK | Mon. | Tues. | Wed. | Thurs. | Fri. | Sat. | Sun. | PLAN Visits,Hr | DONE Visits,Hr |
|---|---|---|---|---|---|---|---|---|---|
| 1 | Feb 11,97 Intake | 2/12 SOC RN HHA 9A-11A(2) HHA 9:30A-11:30A (2) 485 SN-IAP | 2/13 RN HHA 9A-11A(2) DO CC | 2/14 RN HHA 9A-11A(2) 487 | 2/15 RN HHA 9A-11A(2) SW | 2/16 HHA 9A-11A(2) DO CMN | 2/17 | RN(3) HHA(4)(8) SW(1) | RN(3) HHA(4)(8) SW(1) |
| 2 | 2/18 RN HHA 9A-11A(2) HHA 9A-10A | 2/19 HHA 9A-11A(2) MED | 2/20 RN HHA 9A-11A(2) CC | 2/21 HHA 9A-11A(2) IR DO | 2/22 RN HHA 9A-11A(2) HHA 9A-11:30A (2.5) | 2/23 HHACPU LAB REPORT DUE | 2/24 | RN(3) HHA(5)(10) | RN(2) HHA(5)(10.5) |
| 3 | 2/25 RN HHA 9A-11A(2) SV REPORT DUE | 2/26 RN HHA 9A-11A(2) | 2/27 RN HHA 9A-11A(2) CC | 2/28 HHA 9A-11A(2) | March 1,97 RN HHA 9A-11A(2) | 3/2 RN DO | 3/3 | RN(3) HHA(5)(10) | RN(3) HHA(5)(9) |
| 4 | 3/4 RN | 3/5 HHA 9A-11A(2) | 3/6 RN CC CMN | 3/7 RN HHA 9A-11A(2) MED | 3/8 RN CS | 3/9 HHA 9A-11A(2) MED | 3/10 DS | RN(3) HHA(5)(10) | RN(2) HHA(2)(4) |

CLIENT INFORMATION

Chart: 014645
Breedlove, Sarah Jane                          Physician: Dr. John Gentletouch Referred by: Vicksburg Health Clinic - Mattie Johns, SW 555-1212 ext. 1234
   Admitted: 02/16-98 Discharged:

Address: 90494 Vegetable Drive
            Shampoo, Indiana 49404-4432         (555)555-4405

Primary Care:
   Physician: Dr. John Gentletouch
              222 Cotton Tip Lane               Mobile medi-van: on the road after
              Softy City, TN 35477              regular office hours. See number below.
              (770)777-1297                     Pager: 707-1270

Significant Contact: Mae Perry Bundles          Relationship: Daughter
                     1234 12th Street
                     Harlem, NY 04443-4493      Phone# 1: (555) 555-3321
                                                Phone# 2: work - 345-4452

Personal:   DOB: 02/11/12    Age: 86  Female           SS#: 940-40-2345
   Nationality: African-American          Marital Status: Divorced Employment: Employed                               Current: Business Owner
               Retired                                Previous: Domestic

MATCH TO FIG. 15A2

MATCH TO FIG. 15A1

```
Primary Payor:  Medicare                              Policy#:
  Medicare#:    940-40-2345 A                         Group#:
  Medicaid#:
     Claim#:

Directions to Home:  Take Green Road to Morningstar, go north
                     Take Morningstar to Sun Store, turn left
                     Take Sun Store to Vegetable Drive, turn right
                     The house is on a culdesac
                     Use the side door and knock loud, the doorbell does not work Ordered Services:    RN          Assessment and teaching
                     PT/PTA      Assessment and evaluation
                     OT/OTA      Assessment and evaluation
                     SLP         Assessment and evaluation
                     SW/SWA      Assessment and evaluation
                     HHA/PC      Personal Care and ADL Safety Measures:  No throw rugs
                  Standard universal precuations and safety measures Allergies:  No Known Allergies Nutrition:  1800 calorie ADA
         O: Low Fat
         O: Low Salt
         O: No Added Sugar
```

*Fig. 15A2*

```
Chart: 014645                               Physician: Dr. John Gentletouch           continued...
Breedlove, Sarah Jane DME:  Blood glucose monitoring machine
               Bedside commode
               Cane (standard)
               Hospital bed, electric and semi-electric controls
               Oxygen
               Oxygen related equipment
               Walker (standard)

Use Happy Sam's DME at 555-4444 ask for the guy named Sam, he's happy...
               Wheelchair Funct. Limitation: Hearing Impaired, Dyspnea min. exertion, Ambulation (altered), Endurance Limited Activities Permitted: Wheelchair, Walker, Up as tolerated, Cane Mental Status: Oriented, Depressed, Agitated Prognosis: Fair Additional Info: Referred from Dr. Gentletouch via hospital clinic. Pt was at the clinic and
                   spiked a BP of 196/106. BP decreased while at the clinic but the Dr. wanted
                   follow up and close attention paid to her CHF and Angina. She had also
                   experienced some lightheadedness and some falls and she has had some problems
                   that require an evaluation from the allied therapies (OT, PT, SW and SLP)
```

*End of Report*

*Fig. 15B*

Fig. 16A  HISTORY AND PHYSICAL

Chart: 014645
Breedlove, Sarah Jane                     Physician: Dr. John Gentletouch

| | |
|---|---|
| Principal Diagnosis: | 11/18/96: [ICD9 - 428.0] Congestive Heart Failure (CHF) |
| Surgical Diagnosis: | |
| Other Diagnosis: | 11/01/96: [ICD9 - 413.9] Angina Pectoris (Unstable)<br>05/19/82: [ICD9 - 250.0] Diabetes Uncomplicated<br>03/08/97: [ICD9 - 401.9] Hypertension |
| Pertinent History: | 86 yo BF with Hx. of cardiovascular trouble has recently experienced problems with her health for which the Dr. wants ongoing assessment and evals. |
| Sensory: | Hearing Impaired, Glasses, Cateracts<br>Her cateracts are not yet "ripe" |
| Neurological/Mental: | Oriented, Depressed, Agitated, Syncope, Headache<br><br>Have Psych Nursing services been ordered or indicated?   No<br><br>She has had some depression about her recent health condition and she has also had some lightheadedness possibly d/t her HTN |
| Respiratory: | Dyspnea/SOB, Cough, Oxygen, Othopena, Rales<br><br>There are rales in the lower bases and she has a hx of second hand smoke.<br>Her cough is dry and non productive. |

MATCH TO FIG.16B

MATCH TO FIG.16A

Cardiovascular: Chest, Pain, Dysrythmia, Murmur, Variscocities, Palpitations, Edema, Neck Vein Distension, Poor Peripheral Pulse, Hypertension She has had runs of PVC's without notice, c/o of an occas. chest thrill. She has +2 pitting edema b/l in the lower extremities Digestive: Constipation, Incontinence, Anorexia, Swallowing Difficulty Appetite has decreased since she has expressed problems swallowing. Uses laxatives d/t hx of frequent episodes of hard stools Genitourinary: Incontinence Occas bedwetting d/t urgency and not enough time to get to the BR Endocrine: Hypoglycemic Signs/Symptoms, Hyperglycemic Signs/Symptoms, Weight Loss Hx of NIDDM, diet and intake sugar monitored closely. She has a home glucometer and checks her BS weekly.

Skin: WNL

Musculoskeletal: Poor Strength, Swelling, Pain, ROM - Limited, Poor Coordination, Tingling Coordination has decreased in the past year. Swelling in lower extremities. c/o joint pain upon walking.

Wound: None

\*\*\*End of Report\*\*\*\*

*Fig. 16B*

Fig. 17A1 HOME HEALTH CERTIFICATION AND PLAN OF CARE (485)

| Patient's HI Claim No. | Start of Care | Certification Period | | Medical Record No. | Provider No. |
|---|---|---|---|---|---|
| 940-40-2345 A | 021698 | From: 021698 | To: 041698 | 014645 | 45-4444 |

Patient's Name and Address:
Sarah Jane Breedlove
90494 Vegetable Drive, Shampoo, Indiana, 49404-4432

Provider's Name, Address and Telephone No.
Happy Home Health
1234 Any Street, Cleveland, Ohio 74574-4444
(216) 248-7650  (216) 439-8121

Date of Birth: 021112 | Sex: Female

ICD-9-CM / Principal Diagnosis / Date    11/18/96: [ICD9-428.0] Congestive Heart Failure (CHF)

ICD-9-CM / Surgical Procedure / Date

ICD-9-CM / Other Pertinent Diagnoses / Date   11/01/96: [ICD9-413.9] Angina Pectoris (Unstable)
05/18/82: [ICD9-250.0] Diabetes Uncomplicated
03/08/97: [ICD9-401.9] Hypertension Functional Limitations
1. Amputation ☐   5. Paralysis ☐   9. Legally Blind ☐
2. Bowel/Bladder ☐   6. Endurance ☒   A. Dyspnea ☒
3. Contracture ☐   7. Ambulation ☒   B.
4. Hearing ☒   8. Speech ☐
B. Other:

1. Complete Bedrest ☐   5. Exercise Prescribed ☐   9. Cane ☒
2. Bedrest BRP ☒   6. Part'l Weight Bearing ☐   A. Wheelchair ☒
3. Up As Tolerated ☒   7. Independent At Home ☐   B. Walker ☒
4. Trans. Bed/Chair ☐   8. Crutches ☐   C. No Restrictions ☐
D: Other:

Mental Status    1. Oriented ☒   2. Comatose ☐   3. Forgetful ☐   4. Depressed ☒   5. Disoriented ☐
6. Lethargic ☐   7. Agitated ☒   8. Other ☐

She has had some depression about her recent health condition and she has also had some lightheadedness d/t her HTN

MATCH TO FIG.17A2

| Prognosis | 1. Poor ☐ | 2. Guarded ☐ | 3. Fair ☒ | 4. Good ☐ | 5. Excellent ☐ |
|---|---|---|---|---|---|
| | 6. Other ☐ | | | | |

| Medications | 2/10/98 MOM1 TBSP qid.prn po |
|---|---|
| | 2/11/98 Metamucil 2 TBSP qam po, in OJ |
| | 2/13/98 Tylenol (acetaminophen) 2 tabs qid, prn po |
| | 2/5/97 Xanax (Alprazolam) .025 mg qhs po |
| | 3/8/97 Tenormin (Atenolol) 25 mg tid po |
| | 3/9/97 Capoten(Catopril) 25 mg tid po |
| | 4/10/96 Lasix (Furosemide) 20 mg tid po |

| DME and Supplies | Blood glucose monitoring machine |
|---|---|
| | Bedside commode |
| | Cane (standard) |
| | Hospital Bed, electric & semi-electric controls |
| | Oxygen |
| | Oxygen related equipment |
| | Walker (standard) |
| | Use Happy Sam's DME at 555-4444 ask for the guy named Sam, he's happy... |
| | Wheelchair |

| Safety Measures | No throw rugs |
|---|---|
| | Standard universal precautions and safety measures |

| | |
|---|---|
| Nutritional Requirements | 1800 Calorie ADA<br>Low Fat<br>Low Salt<br>No Sugar Added |
| Allergies | No Known Allergies |
| Orders and Treatments | Skilled Nursing Visit Pattern: 2wk4;1wk4<br><br>1101 Assess Respiratory rate, rhythm, ease and depth, chest palpitation and percussion<br>1102 Assess Lung sounds: rales, bronchi, wheezing, rubs<br>1103 Assess Dyspnea with or without exertion/exercize<br>1104 Assess Orthopnea and tacypnea<br>1109 Assess Edema/fluid retention<br>1111 Assess Fatigue, restlessness and confusion<br>1112 Assess Ability for personal care, independence and self-care limitations<br>1115 Assess Nutrition status and special diets<br>1116 Assess Hydration status/fluid intake (I&O)<br>1117 Assess Medication effectiveness and compliance<br>1200 Skilled Complete Cardiovascular Assessment<br>1201 Assess Heart rate/apical pulse, rhythm, irregularity, palpitations, gallops and murmurs<br>1202 Assess Blood Pressure<br>1203 Assess Chest symmetry<br>1204 Assess Chest pain/tightness: aggravating and relieving factors<br>1205 Assess Pain: arms, throat, jaw, extremities<br>1206 Assess Jugular (Neck) vein distention<br>1207 Assess Lower Extremities: edema, numbness, tingling, discoloration, coldness, ulcers, varicose veins, pedal pulses<br>1208 Assess Peripheral pulses<br>1209 Assess Homan's sign |

MATCH TO FIG.17B2

MATCH TO FIG.17B1

| | |
|---|---|
| 1210 | Assess Factors that aggravate vital signs (BP/P/R) |
| 1211 | Assess Factors that give relief fo cardiac distress symptoms |
| 1212 | Assess Anxiety, stress |
| 1213 | Assess Headache, change in mentation, dizziness, lightheadedness, weakness, fainting |
| 1214 | Assess Insomnia |
| 1215 | Assess Skin color: pallor, redness, flushing, cyanosis, clamminess |
| 1216 | Assess Skin texture: turgor, dryness, moistness, diaphoresis, temp., capillary refill |
| 1217 | Assess Weight increase and decrease |
| 1218 | Assess Nausea, vomitting |
| 1219 | Assess Appetite, anorexia |
| 1131 | Teach Regarding Medications: functions, instructions, amount, regimen, schedule, storage, side effects, contraindications and delivery |
| 1137 | Teach regarding Nutritional (food and fluid) intake and restrictions |
| 1138 | Teach regarding Energy conservation measures/planning rest periods/avoid exacerbations |
| 1139 | Teach regarding Best position during sleep for optimal breathing |
| 1140 | Teach regarding Effects of exertion and exercize on breathing |
| 1141 | Teach regarding Tobacco consumption |
| 1142 | Teach regarding Alcohol consumption/use |
| 1143 | Teach regarding Signs and symptoms of their disease/illness/condition |
| 1230 | Teach family and/or client pertinent areas concerning cardiovascular illness |
| 1231 | Teach regarding Proper use cardiac medications |
| 1232 | Teach regarding Special diet instructions: low fat, low cholesterol, low sodium |
| 1233 | Teach regarding Symptom management and proper response to discomfort |
| 1234 | Teach regarding Sleeping/resting positions: head elevated, feet elevated |
| 1235 | Teach regarding Relaxation, stress and anxiety reducing activity |
| 1236 | Teach regarding Thrombolytic therapy (if needed) |
| 1237 | Teach regarding Home IV therapy (if needed) |
| 1238 | Teach regarding cardiovascular related procedures |
| 1239 | Teach regarding Cardiac related lab tests |
| 1240 | Teach regarding Cardiac rehabilitation and recovery program |

| |
|---|
| 1241 Teach regarding Use of antiembolism stockings |
| 1242 Teach regarding Issues regarding sexuality |
| 1243 Teach regarding Daily recording and logs of pulse, weights, I & O, activity |
| 1039 Teach use of home glucometer machine |
| |
| Home Health Aide Visit Pattern: 3-5 wk 9 |
| |
| 3000 Personal Care and ADL |
| 3100 Bathing |
| 3200 Skin, Hair and Nail Care |
| 3300 Mouth/Oral Care |
| 3400 Elimination Assistance/Incontinence Care |
| 3500 Meal Preparation/Assistance |
| 3600 Housekeeping/Homemaking |

| | |
|---|---|
| Goals | 102: Adhere to the plan of care by client and caregiver |
| | 105: Blood pressure within normal range DB <100  SBP <200 if over notify the Dr. |
| | 111: Edema resolved |
| | 113: Effective personal care and ADL |
| | 114: Improved cardiovascular status |
| | 122: Medication control |
| | 125: Nutritional needs addressed and maintained |
| | 128: Patient and family educational needs met |
| | 129: Patient maintained in the home safely |
| | 138: Stable respiratory and cardiovascular status |

MATCH TO FIG. 17C2

MATCH TO FIG.17C1

300: ADL Assistance
301: Effective personal care and hygiene
302: Patient clean and comfortable
303: Safe home environment

| Rehab. Potential | Fair | |
|---|---|---|
| Discharge Plans | Discharge when goals are met, if not, recertify after authorization period is up | |
| Nurse's Signature and Date of Verbal SOC Where Applicable: | | Date HHA Received Signed POT |
| Physician's Name and Address:<br><br>Gentletouch, John<br>222 Cotton Tip Lane<br>Softy City, TN 35477 | I certify/recertify that this patient is confined to his/her home and needs intermittent skill nursing care, physical therapy and/or speech therapy or continues to need occupational therapy. The patient is under my care, and I have authorized the services on this plan of care and will periodically review the plan. | |
| Attending Physician's Signature and Date Signed: | Anyone who misrepresents, falsifies or conceals essential information required for a payment of Federal funds may be subject to fine, imprisonment, or civil penalty under applicable Federal laws. | |

ADDENDUM TO PLAN OF CARE AND MEDICAL UPDATE (487)

| Patient's HI Claim No. | Start of Care | Certification Period | | Medical Record No. | Provider No. |
|---|---|---|---|---|---|
| 940-40-2345 A | 021698 | From: 021698 | To: 041698 | 014645 | 45-4444 |

| Patient's Name | Provider's Name |
|---|---|
| Sarah Jane Breedlove | Happy Home Health |

Visit Pattern  1 wk 2
Orders  4000 Home Physical Therapy Treatment
        4001 Evaluation (Physical Therapy)
        4002 Endurance training
        4003 General conditioning
        4004 Home Safety Assessment
        4005 Muscle strengthening program
        4006 Gait training
        4007 Home exercise program with ROM, teaching and implementation
        4008 Evaluate and teach safe use of assistive devices and DME: walker, cane and WC
        4009 Progressive exercise program, teaching and implementation
        4010 Therapeutic exercise program, teaching and implementation
        4011 Therapeutic massage
        4012 Teach injury prevention and safety precautions (falls, home hazards)
        4013 ADL assessment and training
        4014 Manage and evaluate plan of care
        4015 Supervise assistant staff

MATCH TO FIG. 18A2

MATCH TO FIG. 18A1

Goals:
450 Conditioning, strengthening and functional use of prosthesis
451 Daily exercise regimen compliance
452 Function maintained
454 Gait compliance
456 Increased and safe mobility
457 Increased balance, mobility, function and independence
458 Increased conditioning and strengthening
459 Increased endurance
460 Increased endurance for ambulation
463 Patient compliant with home exercise program
464 Patient utilizing conservation of energy techniques and other skills taught

| Signature of Physician | Date |
|---|---|
| Optional Name/Signature of Nurse/Therapist | Date |

ADDENDUM TO PLAN OF CARE AND MEDICAL UPDATE (487)

| Patient's HI Claim No. | Start of Care | Certification Period | | Medical Record No. | Provider No. |
|---|---|---|---|---|---|
| 940-40-2345 A | 021698 | From: 021698 | To: 041698 | 014645 | 45-4444 |
| Patient's Name | | | Provider's Name | | |
| Sarah Jane Breedlove | | | Happy Home Health | | |

Visit Pattern   1 visit

Orders
5000  Home Occupational Therapy Treatment
5001  Evaluation (Occupational Therapy)
5002  Endurance training
5003  General conditioning
5004  Home Safety Assessment
5005  Muscle strengthening program
5006  Encourage independence and self-care
5007  Home exercise program with ROM, teaching and implementation
5008  Evaluate and teach safe use of assistive devices and DME <specify DME>
5009  Progressive exercise program, teaching and implementation
5010  Therapeutic exercise program, teaching and implementation
5011  Therapeutic massage
5012  Teach safety precautions
5013  ADL assessment and training and re-training
5014  Manage and evaluate plan of care
5015  Supervise assistant staff

MATCH TO FIG.18B2

MATCH TO FIG.18B1

Goals: 450 Conditioning, strengthening and functional use of prosthesis
451 Daily exercise regimen compliance
452 Function maintained
457 Increased balance, mobility, function and independence

| | Date |
|---|---|
| Signature of Physician | |
| Optional Name/Signature of Nurse/Therapist | Date |

Fig. 18B2

DOCTORS ORDERS

Chart: 014645                Physician: Dr. John Gentletouch
Breedlove, Sarah Jane 02/16/98  By: Jetson, George
          Pt. needs a new wheelchair. Order from Happy Sam's DME
          after measuring and fitting is complete 02/16/98  By: Piggy, Miss
          Discharge client from OT services. Eval and teaching done.

*End of Report*

VISITS

Chart: 014645          All Disciplines          From: 02/16/98          TO: 12/19/98
Breedlove, Sarah Jane

| 12/19/98 | 5:00PM - 6:20PM | Mileage: 6 | Visit By: Piggy, Miss    Staff OT |
| Temp: | deg F    oral    Pulse:    Resp:    BP:    /    Weight:    lbs |

Supplies:

Skills: 5000 Home Occupational Therapy Treatment
9500 Occupational Therapy Initial Assessment: Complete H&P, Head to Toe Assessment,
Home Safety Assessment, Establish Visit Pattern, Coordinate Care of Assistants (if needed)

02/16/98    4:51PM    Exercise teaching done and no need for additional visits

| 12/19/98 | 10:00AM - 11:30AM | Mileage: 11 | Visit By: Rubble, Betty    Home Health Aide |
| Temp: | deg F    oral    Pulse:    Resp:    BP:    /    Weight:    lbs |

Supplies: Latex Gloves
Light Blue Pads
Washing Cloth

Skills: 3000 Personal Care and ADL
3103 Bedside Bath
3200 Skin, Hair and Nail Care
3202 Comb / Brush Hair
3204 Massage / Back Rub
3300 Mouth / Oral Care
3301 Natural Teeth Care
3302 Denture Care
3500 Meal Preparation / Assistance
3600 Housekeeping / Homemaking

02/16/98    5:05PM

| 02/18/98 | 10:05AM - 11:10AM | Mileage: 18 | Visit By: Jones, Michelle    Registered Nurse |

*MATCH TO FIG. 20A2*

MATCH TO FIG.20A1

| Temp: 98.2 deg F | Pulse: 76 | Resp: 16 | BP: 180 / 90 | Weight: lbs |
|---|---|---|---|---|

Supplies:
Skills:
1200 Skilled Complete Cardiovascular Assessment
1100 Skilled Complete Respiratory Assessment
1131 Teach regarding Medications: functions, instructions, amount, regimen, schedule, storage, side effects, contraindications and delivery
1201 Assess Heart rate/apical pulse, rhythm, irregularity, palpitations, gallops and murmurs
1202 Assess Blood Pressure
1204 Assess Chest Pain/tightness: aggravating and relieving factors
1205 Assess Pain: arms, throat, jaw, extremities
1207 Assess lower extremities: edema, numbness, tingling, discoloration, coldness, ulcers, varicose veins, pedal pulses
1208 Assess Peripheral Pulses
1231 Teach regarding Proper use of cardiac medications
1232 Teach regarding Special diet instructions: low fat, low cholesterol, low sodium 02/16/98  5:05PM  A & Ox3, lungs with rales in the lower bases b/l otherwise clear. Resp. easy and unlabored unless she is walking 10 ft. At 10 ft. she becomes SOB. Heart sounds reg. no s3 or s4. She c/o of some sl. chest pain, but did not take any nitro tabs. Abd. is large, soft and round without palpable or visible masses. Nontender with bx4, she states her appetite has decreased since she has had problems swallowing. Skin is W/D, with a brisk capillary refill and good turgor. Her RBS checked with the glucometer is 154.

| 02/17/98 | 2:20PM - 3:50PM | Mileage: 9 | Visit By: Jetson, George | Staff PT |
|---|---|---|---|---|
| Temp: deg F | oral | Pulse: | Resp: | BP: / | Weight: 205.00 lbs |

Supplies:
Skills:
4000 Home Physical Therapy Treatment
9400 Physical Therapy Initial Assessment: Complete H&P, Head to Toe Assessment, Home Safety Assessment, Establish Visit Pattern, Coordinate Care of Assistants

*Fig. 20A2*

Chart: 014645               All Disciplines
Breedlove, Sarah Jane                                    From: 02/16/98       TO: 12/19/98

| 02/16/98 | 4:26PM | Called Dr. to establish plan. Exercise plan discussed with client. She was very agreeable. |
| 02/16/98 | 4:27PM | She needed a new WC because the old WC was not properly fitted. |

02/16/98   2:00PM - 3:35PM    Mileage: 22    Visit By: Jones, Michelle    Registered Nurse
Temp: 98.6 deg F   oral    Pulse: 88    Resp: 22    BP: 178 / 98    Weight: 204.00 lbs
Supplies:
Skills: 9000 Initial Admission Requirements: Obtained signature forms. Taught regarding Advanced
        Directives, Home Care Bill of Rights and Consent For Treatment. Established communication
        folder in the home. Coordinated other disciplines (as ordered)
        9100 Skilled Nursing Initial Assessment: Complete H & P, Head to Toe Assessment, Home
        Safety Assessment, Nutrition Assessment, Medication Assessment 02/16/98   3:36PM   86 yo BF with Hx of cardiac problems, angina and HTN and CHF seen today for an
                    initial assessment. A & 3, lungs with rales in the lower bases b/l otherwise
                    clear. Resp easy and unlabored unless she is walking lo ft.. At 10 ft she
                    becomes SOB. She is dependent on a cane, walker or furniture for balance.
                    Abd. is large, soft and round without palpable or visible masses. Nontender
                    with BSx4. she states her appetite has decreased since she has had problems
                    swallowing. Skin is W/D, with a brisk capillary refill and good turgor. Her
                    meds were reviewed and a home care plan was discussed. She is looking forward
                    to the help she will be receiving. She does not want any visits before
                    10:00AM as she sleeps in late. She states that her neighbor comes in to check
                    on her daily and that her daughter is available by phone anytime. Her RPS
                    checked with the glucometer is 162. She states that it rarely goes to 200.

02/16/98   3:41PM   Lower extremities are edematous with +2 pitting edema b/l.

* End of Report *

MEDICATIONS

Chart: 014645         All Disciplines         From: 02/16/98         TO: 12/19/98
Breedlove, Sarah Jane Allergies: No known allergies                         Pharmacy: CJ Pharmacy
                                                      Ph#.  (555)555-9324

04/10/96   Lasix (Furosemide)                20    mg    tid   po (water pills) Action: Increases sodium loss and increases water loss. Decreases water reabsorption in the kidneys. Reduced blood pressure. Side effects / adverse reactions: Hypokalemia, anemia, dehydration, hyponatremia, diarrhea, decreased appetite, flushing, headache, nervousness, rash, orthostatic hypotension 02/15/97   Xanax (Alprazolam)                .025  mg    qhs   po (anxiety) Action: Calming effect, increases dopamine. Side effects / adverse reactions: Laryngospasm, dyspnea, postural hypotension, hypertension, cardia arrest, seizures, drowsiness, headache, confusion, agitation, nervousness, anxiety, insomnia, dizziness, depression, constipation, blurred vision, impotence, urinary retention 03/08/97   Tenormin (Atenolol)               25    mg    tid   po (blood pressure control) Action: Vasodilation of peripheral blood vessels, decreases impulses in the sympathetic nervous system, inhibits vasoconstriction, depletes dopamine, decreases norepinepherine. Side effects / adverse reactions: Marked hypotension, bradycardia, tachycardia, headache, N/V, nasal congestion, eczema, glaucoma, angina, sedation, weakness

MATCH TO FIG. 21B

MATCH TO FIG. 21A

| Date | Medication | Dose | Unit | Freq | Route | Details |
|---|---|---|---|---|---|---|
| 03/09/97 | Capoten (Catopril) | 25 | mg | tid | po | (heart, chest pain) Actiob: Relaxes and dilates coronary vessels and cardiac smooth muscle. Side effects / adverse reactions: Rash, abdominal pain, tachycardia, erythmia, hypotension, dizziness, weakness, N/V |
| 02/10/98 | MOM | 1 | TBSP | qid, prn | po | (heartburn, gastric trouble) Action: Neutralizes gastric acid. Decreases the rate of gastric emptying. Side effects / reactions: Constipation, fecal and bowel impaction, abdominal pain, distension, diarrhea, belching, flatulence, electrolyte imbalance |
| 02/11/98 | Metamucil | 2 | TBSP | qam | po, in OJ | Action: Irritates the intestinal mucosa, adds fatty substances, retains water, lubricates intestine. Side effects / reactions: Cramps, electrolyte imbalance, rash, N/V, intestinal obstruction, lower abdominal pain and cramping |
| 02/13/98 | Tylenol (Acetaminophen) | 2 | tabs | qid, prn | po | (pain control) Action: Decreases neural impulses thereby decreasing pain. Side effects / adverse reactions: Decreased appetite, dry mouth, constipation, decreased urinary output, urinary retention, flushing, tachycardia, hypertension, dizziness, sedation, headache, decreased respirations, asthma, seizures, liver disease, weakness, N/V |

\*\*\* End of Report \*\*\*\*

*Fig. 21B*

LAB TESTS & RESULTS

Chart: 014645  
Breedlove, Sarah Jane  
Physician: Dr. John Gentletouch

| Date | Test | Value | Status |
|---|---|---|---|
| 02/16/98 | Glucose (random) 65-110 mg/dL<br>Higher than normal, but avg. for pt. | 162 | abnormal |
| 02/16/98 | Glucose (fasting) 65-110 mg/dL<br>Higher than normal, but avg. for pt. no instructions given. | 154 | abnormal |

* End of Report *

*Fig. 22*

CASE COMMENTS

Chart: 014645  
Breedlove, Sarah Jane  
Physician: Dr. John Gentletouch

| Date | Comment | Value | Status |
|---|---|---|---|
| 02/16/98 | By: Jones, Michelle<br>BP called to Dr. Gentletouch. No orders given. | 162 | abnormal |

* End of Report *

HHA CARE PLAN

Chart: 014645
Breedlove, Sarah Jane
Updated: 02/16/98  04:16:21PM

Physician: Dr. John Gentletouch

Address: 90494 Vegetable Drive  Ph#. (555)555-4405
Shampoo, Indiana 49404-4432

Contact: Mae Perry Bundles  Ph#. (555)555-3321

Directions: Take Green Road to Morningstar, go north
Take Morningstar to Sun Street, turn left
Take Sun Street to Vegetable Drive, turn right
The house is on a culdesac
Use the side door and knock loud, the doorbell does not work Entry Instructions: Front door (now that the steps have been repaired)

Parking Instructions: Park on the street. She does not want the driveway blocked.

Service Rooms: Only deliver services in the bedroom, bathroom and kitchen. She has had bad experiences with hha's who have stolen from her Roommates: Her daughter lives in another state, but her neighbor checks on her daily Pets: No Allergies: No known allergies Medical Equipment: Blood glucose monitoring machine
Bedside commode
Cane (standard)
Hospital bed, electric and semi-electric controls
Oxygen
Oxygen related equipment
Walker (standard)

MATCH TO FIG.24A2

```
MATCH TO FIG.24A1
                        Use Happy Sam's DME at 555-4444 ask for the guy named Sam, he's happy....
                        Wheelchair Mental Status:  Oriented, depressed, agitated, Syncope, Headache She has had some depression about her recent health condition and she
                        has also had some lightheadedness possibly d/t her HTN Diversional Activity:  She reads the Bible and listens to Gospel music
        Hearing/Vision: Hearing impaired, glasses, cateracts
                        Her cateracts are not yet "ripe"

Functional Ability.....
        Walking Ability:       With Assistance
        Getting out of Bed:    With Assistance
        Sitting/Standing:      With Assistance
        Toileting/Elimination: With Assistance
        Dressing:              With Assistance
        Medication:            With Assistance
        Comments:              Remind about Medication. Assist with transfers. Remove tripping hazards..

Range of Motion.....
        Upper Body: Limited
        Lower Body: Limited

Skills.....
             Bathing: Partial Bed Bath, Shower (chair)
   Skin/Hair/Nail Care: Shampoo, Lotion Skin, Comb/Brush Hair, File/Clean Nails, Massage/Back Rub
       Mouth/Oral Care: Natural teeth, Denture / Partial Care
```

*Fig. 24A2*

```
HHA CARE PLAN

Chart:  014645
Breedlove, Sarah Jane                    Physician: Dr. John Gentletouch
Updated:    02/16/98   04:16:21PM                              continued....

Incontinent Care: Change Chux (Blue Pads)

Nutritional Requirements: 1800 Calorie ADA
                          Low Fat
                          Low Salt
                          No Sugar Added Meal Preparation: Cook/Prepare/Serve, Special Diet, Food Restrictions
          Housekeeping: Straighten client's area, Damp mopping, Trash bagging, Dust, Vacuum,
                        Laundry, Wash dishes, Linen change, Sweeping Additional Instructions: WHENEVER A CHANGE IS MADE ON THE HOME HEALTH AIDE CARE PLAN A NEW HHA
                         CARE PLAN IS CREATED AND THE "UPDATE" DATE APPEARS AT THE TOP OF THE
                         HHA CARE PLAN TO SHOW A HISTORY.

Her neighbor checks on her. If she needs you to run an errand, the neighbor
                         handles the finances. The neighbor's name is Anne Hall and her phone
                         number is 555-3434.
```

HHA CARE PLAN

Chart: 014645
Breedlove, Sarah Jane
Updated: 02/16/98   03:28:30PM

Physician: Dr. John Gentletouch    Ph#. (555)555-4405 continued...

- Address: 90494 Vegetable Drive
  Shampoo, Indiana  49404-4432
- Contact: Mae Perry Bundles    Ph#. (555)555-3321
- Directions: Take Green Road to Morningstar, go north
  Take Morningstar to Sun Street, turn left
  Take Sun Street to Vegetable Drive, turn right
  The house is on a culdesac
  Use the side door and knock loud, the doorbell does not work
- Entry Instructions: Side door
- Parking Instructions: Driveway
- Service Rooms: All
- Roommates: Her daughter lives in another state, but her neighbor checks on her daily
- Pets: No
- Allergies: No known allergies
- Medical Equipment: Blood glucose monitoring machine
  Bedside commode
  Cane (standard)
  Hospital bed, electric and semi-electric controls
  Oxygen
  Oxygen related equipment
  Walker (standard)

MATCH TO FIG. 24C2

MATCH TO FIG.24C1

Use Happy Sam's DME at 555-4444 ask for the guy named Sam, he's happy....
Wheelchair Mental Status: Oriented, Depressed, Agitated, Syncope, Headache She has had some depression about her recent health condition and she
has also had some lightheadedness possibly d/t her HTN Diversional Activity: She reads the Bible and listens to Gospel music
Hearing/Vision: Hearing impaired, glasses, cateracts
Her cateracts are not yet "ripe".

Functional Ability.....
  Walking Ability: With Assistance
  Getting out of Bed: With Assistance
  Sitting/Standing: With Assistance
  Toileting/Elimination: With Assistance
  Dressing: With Assistance
  Medication: With Assistance
  Comments: Remind about Medication. Assist with transfers. Remove tripping hazards.

Range of Motion.....
  Upper Body: Limited
  Lower Body: Limited

Skills.....
  Bathing: Partial Bed Bath, Shower (chair)
  Skin/Hair/Nail Care: Shampoo, Lotion Skin, Comb/Brush Hair, File/Clean Nails, Massage/Back Rub
  Mouth/Oral Care: Natural teeth, Denture / Partial Care
  Incontinent Care: Change Chux (Blue Pads)

HHA CARE PLAN

Chart: 014645  
Breedlove, Sarah Jane   Physician: Dr. John Gentletouch  
Updated:  02/16/98   03:28:30PM                                           continued....

Nutritional Requirements: 1800 Calorie ADA  
                         Low Fat  
                         Low Salt  
                         No Sugar Added Meal Preparation: Cook/Prepare/Serve, Special Diet, Food Restrictions Housekeeping: Straighten client's area, Damp mopping, Trash bagging, Dust, Vacuum, Laundry, Wash dishes, Linen change, Sweeping Additional Instructions: Her neighbor checks on her. If she needs you to run an errand, the neighbor handles the finances. The neighbor's name is Anne Hall and her phone number is 555-3434.

\*\*\*End of Report\*\*\*

Fig. 25

SUPERVISORY VISITS

Chart: 014645  
Breedlove, Sarah Jane   Physician: Dr. John Gentletouch

02/16/98  By: Jones, Michelle  
          The client is satisfied with the service.  
          The care plan is being followed.  
          The aide was present during the supervisory visit.  
          Pt. is happy with her aide services. Pt.'s hygiene status is good.  
          The house is clean and the pathways are clear.

\*\*\*End of Report\*\*\*

*Fig. 26A1*  HISTORY AND PHYSICAL (PT)

Chart: 014645
Breedlove, Sarah Jane                    Physician: Dr. John Gentletouch Principal Diagnosis: 11/18/96: [ICD9 - 428.0] Congestive Heart Failure (CHF)
Surgical Diagnosis:
Other Diagnosis:     11/01/96: [ICD9 - 413.9] Angina Pectoris (Unstable)
                     05/19/82: [ICD9 - 250.0] Diabetes Uncomplicated
                     03/08/97: [ICD9 - 401.9] Hypertension Pertinent History: 86 yo BF needing PT for eval and assessment d/t recent weakness
Complaints: General Discomfort, Intermittent Pain, Aching, Spasms
c/o pain upon walking 10-20 ft. Uses cane, walker and furniture. SOB on exertion.

|  | STRENGTH | | ROM | | | STRENGTH | | ROM | |
|---|---|---|---|---|---|---|---|---|---|
|  | Left | Right | Left | Right |  | Left | Right | Left | Right |
| Shoulder |  |  |  |  | Thumb |  |  |  |  |
| Flexion | 3 | 3 | 3 | 3 | Flexion | 3 | 5 | 3 | 3 |
| Abduction | 2 | 3 | 3 | 3 | Extension | 3 | 3 | 3 | 3 |
| Internal Rotation | 3 | 3 | 2 | 3 | Hip |  |  |  |  |
| External Rotation | 3 | 3 | 3 | 3 | Flexion | 3 | 2 | 3 | 5 |
| Elbow |  |  |  |  | Extension | 5 | 3 | 3 | 4 |
| Flexion | 3 | 1 | 3 | 3 | Abduction | 3 | 3 | -3 | 3 |
| Extension | 3 | 3 | 3 | 3 | Internal Rotation | 3 | 3 | 3 | 2 |
| Supination |  |  |  |  | External Rotation | 3 | 3 | 3 | 4 |

MATCH TO FIG. 26A2

MATCH TO FIG.26A1

| | | | | | | |
|---|---|---|---|---|---|---|
| Wrist | | | | Knee | | |
| Flexion | 3 | 3 | 3 | 2 | Flexion | 0 | 4 | 4 |
| Extension | 3 | 1 | 3 | 3 | Extension | 1 | 4 | 3 |
| Finger | | | | | Ankle | | |
| Flexion | 3 | 3 | 3 | 3 | Dorsi | 4 | 4 | 4 |
| Extension | 3 | 4 | 3 | 3 | Plantar | 4 | 4 | 2 |
| Trunk | | | | | Inversion | 3 | 4 | 3 | 2 |
| Flexion | 4 | 0 | 4 | 1 | Eversion | 4 | 4 | 4 |

Gait Evaluation: Poor strength
Circulation: brisk capillary refill
Weight Bearing: b/l knees can bear little wt.
Assistive Devices: cane and walker
Posture: hunched over
Balance: poor
Skin: WNL
Sensation: can distinguish b/w dull and sharp
Endurance: poor
Cuing Response: not needed, excellent understanding

*Fig. 26A2*

Chart: 014645                              Physician: Dr. John Gentletouch
Breedlove, Sarah Jane                                            continued...

Activities of Daily Living

Dressing: Assistance Needed
      Bathing-Tub: Assistance Needed
          Shower: Assistance Needed
          Eating: Assistance Needed
         Cooking: Assistance Needed
      Ambulation: Assistance Needed
        Toileting: Assistance Needed
        Cleaning: Unable to Perform
       Transfers: Assistance Needed
  W/C Propulsion: Assistance Needed
  Rolling/Turning: Assistance Needed
         Sitting: Assistance Needed
          Stairs: Assistance Needed
   Opening Doors: Independent
 Personal Hygiene: Assistance Needed Teaching Instruction Plan Assessment reveals need for self exercises and ROM. Will see her once more and
        then DC. The HHA can assist with ROM exercises to build endurance.

*End of Report*

HISTORY AND PHYSICAL (OT)

Chart: 014645
Breedlove, Sarah Jane                                  Physician: Dr. John Gentletouch Principal Diagnosis: 11/18/96: [ICD9 - 428.0] Congestive Heart Failure (CHF)
Surgical Diagnosis:
    Other Diagnosis: 11/01/96: [ICD9 - 413.9] Angina Pectoris (Unstable)
                     05/19/82: [ICD9 - 250.0] Diabetes Uncomplicated
                     03/08/97: [ICD9 - 401.9] Hypertension
Pertinent History: 86 yo BF in need of eval and assessment
        Complaints: General Discomfort, Aching, Spasms
                    c/o spasms in her right hand

|  | EVALUATION | | | EVALUATION | |
|---|---|---|---|---|---|
|  | Left | Right | |  Left | Right |
| Shoulder | | | Wrist | | |
|   Abduction | 3 | 2 | | | |
|   Flexion | 3 | 3 |   Flexion | 2 | 3 |
|   Extension | 4 | 3 |   Extension | 2 | 3 |
|   Internal Rotation | 2 | 3 | | | |
|   External Rotation | 3 | 2 | Thumb | | |
| Scapula | | |   Flexion | 2 | 2 |
|   Elevation | 3 | 2 |   Extension | 2 | 2 |
|   Retraction | 3 | 3 | | | |

MATCH TO *FIG. 27A2*

MATCH TO FIG.27A1

| | | | Finger Flexion | | |
|---|---|---|---|---|---|
| Elbow | | | Index | 4 | 4 |
| Flexion | 3 | 2 | Long | 3 | 4 |
| Extension | 3 | 3 | Ring | 4 | 2 |
| | | | Little | 4 | 4 |
| Forearm | | | Finger Extension | | |
| Supination | 2 | 2 | Index | 4 | 4 |
| Pronation | 2 | 2 | Long | 4 | 2 |
| | | | Ring | 4 | 4 |
| | | | Little | 4 | 2 |

Circulation: WNL
Posture: hunched over
Sensation:
Weight Bearing: not on knees
Balance: poor
Assistive Devices: walker, cane, wheelchair
Orientation: alert and oriented
Attention Span: good

Chart: 014645
Breedlove, Sarah Jane                    Physician: Dr. John Gentletouch        continued...

Cuing Response: not needed
Cooperation: fine
Interest: small
Sociability: good
Perserverance: some
Endurance: fair Feeding
    Fork: Assistance Needed
   Spoon: Assistance Needed
   Knife: Assistance Needed
  Glass/Cup: Assistance Needed
  Sandwich: Assistance Needed Dressing
  Bra/T-shirt: Assistance Needed
  Underpants: Assistance Needed
  Pullovers: Assistance Needed
  Cardigans: Assistance Needed
  Trousers: Assistance Needed Grooming
  Hands and Face: Assistance Needed
  Bathing: Assistance Needed
  Hair Care: Assistance Needed
  Brushing Teeth: Independent
  Shave/Makeup: Assistance Needed
  Cleaning Eyeglasses: Unable to Perform Bed Roll
  Sit up from supine: Assistance Needed
  Sitting Balance: Assistance Needed
  Lie down: Assistance Needed

MATCH TO FIG. 27B2

MATCH TO FIG. 27B1

```
              Socks: Unable to Perform
              Shoes: Unable to Perform
       Brace/Splint: Assistance Needed
         Fastening: Assistance Needed
      Use of Closet: Assistance Needed Ambulation
          Standing: Assistance Needed
           Balance: Assistance Needed
           Walking: Assistance Needed Perception
   Bilateral Coord: Assistance Needed
   Crossing Midline: Assistance Needed
       Eye Tracking: Assistance Needed
  R&L Discrimination: Assistance Needed
        Face Puzzle: Independent
   Drawing a Person: Independent
      Clock Drawing: Independent
    Parquetry Puzzle: Independent
               Pegs: Independent
   Geometric Shapes: Independent
         Picture ID: Independent
            Writing: Independent Transfers
         W/C to Bed: Assistance Needed
      W/C to Toilet: Assistance Needed Wheelchair Activity
        Lock/Unlock: Assistance Needed
  Adjust Leg Rests: Assistance Needed
             Propel: Assistance Needed
    Floor Retrieval: Assistance Needed Sensory
     Sharp and Dull: Independent
     Position Sense: Independent
        Temperature: Independent
          Finger ID: Independent
          Object ID: Cuing Required
           Textures: Cuing Required Communication
             Verbal: Independent
            Written: Independent
```

Fig. 27B2

```
Chart: 014645                          Physician: Dr. John Gentletouch
Breedlove, Sarah Jane                                       continued...

Body Parts: Independent
    Teaching Instruction Plan
          Eval done but there seems to be no need for ongoing therapy.
          Exercises taught on assessment visit.
```

*Fig. 27C*

* End of Report **

```
Chart: 014645                          Physician: Dr. John Gentletouch
Breedlove, Sarah Jane                                       continued...

Activities of Daily Life
          Telephone Usage:
               Swallowing:
                  Reading:
           Making Change:
                  Chewing:
         Following Recipes:
         Taking Medications:
                  Hearing Teaching Instruction Plan
```

*Fig. 28B*

* End of Report **

*Fig. 28A1*  HISTORY AND PHYSICAL (SL)

Chart: 014645
Breedlove, Sarah Jane

Physician: Dr. John Gentletouch

Principal Diagnosis: 11/18/96: [ICD9 - 428.0] Congestive Heart Failure (CHF)
Surgical Diagnosis:
Other Diagnosis: 11/01/96: [ICD9 - 413.9] Angina Pectoris (Unstable)
 05/19/82: [ICD9 - 250.0] Diabetes Uncomplicated
 03/08/97: [ICD9 - 401.9] Hypertension Pertinent History:
Reason for Referrel:

Receptive Language
Identification of Common Objects:
Following Commands:

Expressive Language
Reading (Oral and Comprehensive)
Writing Skills (Dictated and Copied)
Verbal Response to Questions
    and Statements:

Communications Skills
    Telephone:
    Family:
    Social:

*MATCH TO FIG.28A2*

Oral Peripheral Exam
  Lips:
  Mandible:
  Teeth:
  Occlusion:
  Palate:
  Uvula:
  Pharnyx:

Oral Motor Exam
  Lips Abducted:
  Lips Adducted:
  Tongue Elevation:
  Tongue Protrusion:
  Tongue Retraction:
  Tongue Lateralization:
  Vellum Elevation:
  P-T-K Forward:
  P-T-K Backward:
  Phoneme Control:
  Assistive Devices:

MATCH TO FIG.28A1

Fig. 28A2

*Fig. 29A*    HISTORY AND PHYSICAL (SW)

| | |
|---|---|
| Chart: 014645<br>Breedlove, Sarah Jane | Physician: Dr. John Gentletouch |
| Principal Diagnosis: 11/18/96: [ICD9 - 428.0] Congestive Heart Failure (CHF)<br>Surgical Diagnosis:<br>Other Diagnosis: 11/01/96: [ICD9 - 413.9] Angina Pectoris (Unstable)<br>05/19/82: [ICD9 - 250.0] Diabetes Uncomplicated<br>03/08/97: [ICD9 - 401.9] Hypertension<br>Pertinent History:<br>Reason for Referral:<br><br>Education:<br>Occupation:<br>Religion:<br>Culture/Tradition:<br>Environment:<br>Safety:<br>Transportation:<br>Ambulation:<br>ADL<br>Nutrition: | |

MATCH TO FIG. 29B

```
                            Dental:
                            Vision:
                           Hearing:

Communication:
             Interaction with Others:
                     Mental Status:
                            Coping:
                          Attitude:

Financial Resources:
                            Income:
                            Assets:
                   Economic Status:
                          Expenses Teaching Instruction Plan
```

* End of Report *

HOME SAFETY ASSESSMENT

Chart: 014645  Physician: Dr. John Gentletouch
Breedlove, Sarah Jane

Any hazards seen from outside of home which could obstruct entry or exit from the home? Yes
There are a few broken steps on the front porch. Family notified.

Does the client live alone? Yes
Her daughter lives in another state, but her neighbor checks in on her daily.

Does the Client have?...

| | |
|---|---|
| Fire / Smoke Alarms | Yes |
| Running Water | Yes |
| Fire Extinguisher | Yes |
| 911 Access | Yes |
| Adequate Trash Disposal | Yes |
| Carbon Monoxide Monitors | No |
| Electricity | Yes |
| Working Telephone | Yes |
| Posted Emergency Phone | Yes |
| Vermin / Insects | No |
| Adequate Heating & Cooling | Yes |
| Adequate Toileting Facilities | Yes |

MATCH TO FIG.30B

MATCH TO FIG.30A

Fall Injury Assessment
Any obvious signs of potential fall     Yes
                      Pathways clear    Yes
Any sharp edged furniture / corners     No
                          Bed rails     Yes
                  Tub / Shower bars     Yes
              Stair climbing required    No Medication Safety
           Any threat of overdose       No
        Any needles in med delivery     No
           Proper needle disposal       No
                     Oxygen use         Yes
         Oxygen safety signs posted     Yes Narrative Home Safety Assessment and Instructions

* End of Report *

*Fig. 30B*

INCIDENTS AND OCCURANCES

Physician: Dr. John Gentletouch

Chart: 014645
Breedlove, Sarah Jane

2/16/98   By: Jones, Michelle
          The incident was reported to the supervisor.
          Incident occured on 02/17/98 approximately at 2:00 AM
          Type of Incident: Physical injury
          Pt's neighbor Anne Hall called to state that the pt. fell out of bed and used her
          LIFELINE button to call for help. When the LIFELINE dispatcher called the neighbor, she
          went to the home and found Sarah on the floor next to the bed. She said that she did not
          fall out of bed, but missed the bed by a few inches and slumped to the floor. She was not
          hurt, but was embarassed that she could not get up on her own to get back into bed.
          No injuries sustained.

* End of Report *

*Fig. 31*

CASE SUMMARIES

Physician: Dr. John Gentletouch

Chart: 014645
Breedlove, Sarah Jane

2/16/98   By: Jones, Michelle
          Case summaries are done every 30-60 days or as set by the agency policy and procedure.
          With DND these summaries can be done by phone with option number seven.

* End of Report *

*Fig. 32*

CASE MANAGER'S COMMENTS

Chart: 014645　　　　　　Physician: Dr. John Gentletouch
Breedlove, Sarah Jane

2/16/98　By: Jones, Michelle
　　　　The Case Manager at a Managed Care Organization or the in-house Case Manager can use this
　　　　space for their notes and comments about the case. Like case comments, it can also be used
　　　　for progress notes, case conferences and ongoing information about the patient.

*End of Report*

Fig. 33

AUDIT PAGE

Chart: 014645　　　　　　Physician: Dr. John Gentletouch
Breedlove, Sarah Jane

Surgical diagnosis

**End of Audit page**

Fig. 35

DISCHARGE SUMMARY

Chart: 014645  
Breedlove, Sarah Jane     Physician: Dr. John Gentletouch

| | |
|---|---|
| Discipline: | RN |
| Discipline: | PT/PTA |
| Discipline: | OT/OTA |
| Discharge Date: | 02/16/98 |
| Prognosis/Rehab Potential: | Good |
| Goals Met: | Yes |
| Functional Ability: | Requires partial assistance / limited supervision |
| Any instructions given at time of discharge? | Yes |
| Candidate for re-hospitalization within 6 months? | No |
| Discharge Instructions: | Teaching done, televisit follow-up, HHA can work with ROM exercises. |
| Discipline: | SLP |
| Discipline: | SW/SWA |

* End of Report *

*Fig. 34*

OUTCOME DATA REPORT

Chart: 014645
Breedlove, Sarah Jane          Physician: Dr. John Gentletouch

11/18/96: [ICD9 - 428.0] Congestive Heart Failure (CHF)

11/01/96: [ICD9 - 413.9] Angina Pectoris (Unstable)
05/19/82: [ICD9 - 250.0] Diabetes Uncomplicated
03/08/97: [ICD9 - 401.9] Hypertension Admitted On 02/16/98                     Last Visit: 12/19/98

Discharged After                         Discharged on 02/16/98

| Goals met by Occupational Therapy | | | | | | |
|---|---|---|---|---|---|---|
| Skilled Nursing | 2 | visits | From | 02/16/98 | To | 02/18/98 |
| Home Health Aide | 1 | visits | From | 12/18/98 | To | 12/18/98 |
| Physical Therapy | 1 | visits | From | 02/17/98 | To | 02/17/98 |
| Occupational Therapy | 1 | visits | From | 12/19/98 | To | 12/19/98 |

*Fig. 36*

\*\*\* End of Report \*\*\*

CALENDAR REPORT

Chart: 014645
Breedlove, Sarah Jane

All Disciplines

| Date | Day of Week | Discipline |
|------|-------------|------------|
| 02/16/98 | Monday | Registered Nurse (RN) |
| 02/17/98 | Tuesday | Physical Therapist/Physical Therapy Assistant |
| 02/18/98 | Wednesday | Registered Nurse (RN) |
|  |  | 2/98   Total Visits:   3 |
| 12/18/98 | Friday | Home Health Aide (HHA) |
| 12/19/98 | Saturday | Occupational Therapist/Occupational Therapy |
|  |  | 12/98   Total Visits:   2 |

Total Visits:   5

* End of Report *

VISIT REPORT

Jones, Michelle                                    Visits From: Beginning  To: Now 02/16/98   2:00PM - 3:35PM    Chart: 014645        Breedlove, Sarah
Temp: 98.6 deg F   oral   Pulse: 88   Resp: 22   BP: 178/98   Weight: 204.00 lbs
Supplies:
Skills:    9000 Initial Admissin Requirements: Obtained signature forms, Taught regarding Advanced Directives, Home Care Bill of Rights and Consent For Treatment, Established communication folder in the home, Coordinated other disciplines (as ordered)
           9100 Skilled Nursing Initial Assessment: Complete H & P, Head to Toe Assessment, Home Safety Assessment, Nutrition Assessment, Medication Assessment

| | | |
|---|---|---|
| 02/16/98 | 3:36PM | 86 yo BF with Hx of cardiac problems, angina and HTN and CHF seen today for an initial assessment. A & 3, lungs with rales in the lower bases b/l otherwise clear. Resp easy and unlabored unless she is walking 10 ft. At 10 ft she becomes SOB. She is dependent on a cane, walker or furniture for balance. Abd. is large, soft and round without palpable or visible masses. Nontender with BSx4, she states her appetite has decreased since she has had problems swallowing. Skin is W/D, with a brisk capillary refill and good turgor. Her meds were reviewed and a home care plan was discussed. She is looking forward to the help she will be receiving. She does not want any visits before 10:00AM as she sleeps in late. She states that her neighbor comes in to check on her daily and that her daughter is available by phone anytime. Her RPS checked with the glucometer is 162. She states that it rarely goes to 200. |
| 02/16/98 | 3:41PM | Lower extremities are edematous with +2 pitting edema b/l. |

*MATCH TO FIG. 38B*

MATCH TO FIG.38A

| Temp: 98.2 deg F | oral | Pulse: 76 | Resp: 16 | BP: 180 / 90 | Weight: lbs |

Supplies:

Skills:
1200 Skilled Complete Cardiovascular Assessment
1100 Skilled Complete Respiratory Assessment
1131 Teach regarding Medications: functions, instructions, amount, regimen, schedule, storage, side effects, contraindications and delivery
1201 Assess Heart rate/apical pulse, rhythm, irregularity, palpitations, gallops and murmurs
1202 Assess Blood Pressure
1204 Assess Chest Pain/tightness; aggravating and relieving factors
1205 Assess Pain: arms, throat, jaw, extremities
1207 Assess lower extremities: edema, numbness, tingling, discoloration, coldness, ulcers, varicose veins, pedal pulses
1208 Assess Peripheral Pulses
1231 Teach regarding Proper use of cardiac medications
1232 Teach regarding Special diet instructions: low fat, low cholesterol, low sodium 02/16/98  5:05PM  A & Ox3, lungs with rales in the lower bases b/l otherwise clear. Resp. easy and unlabored unless she is walking 10 ft. At 10 ft. she becomes SOB. Heart sounds reg. no s3 or s4. She c/o of some sl. chest pain, but did not take any nitro tabs. Abd. is large, soft and round without palpable or visible masses. Nontender with bx4, she states her appetite has decreased since she has had problems swallowing. Skin is W/D, with a brisk capillary refill and good turgor. Her RBS checked with the glucometer is 154.

*Fig. 38B*

\*\*\* End of Report \*\*\*

PHONE INSTRUCTIONS

Instructions for Medications, Labs, 485, 487, HHA Care Plan
Chart: 014645, Sarah Jane Breedlove Chart:

*Fig. 39*

\*\*\* End of Report \*\*\*

BILLING REPORT

Chart: 014645

| # | Date | Time | Employee | | Length |
|---|------|------|----------|---|--------|
| 1 | 02/16/98 | 2:00 PM | Jones, Michelle | | 1:35 |
| 2 | 02/17/98 | 2:20 PM | Jetson, George | Staff PT | 1:30 |
| 3 | 02/18/98 | 10:00 AM | Jones, Michelle | | 1:05 |
| 4 | 12/18/98 | 10:05 AM | Rubble, Betty | Home Health Aide | 1:30 |
| 5 | 12/19/98 | 5:00 PM | Piggy, Miss | Staff OT | 1:20 |

*Fig. 40*

\*\*\* End of Report \*\*\*

PHONE-ASSISTED CLINICAL DOCUMENT INFORMATION COMPUTER SYSTEM FOR USE IN HOME HEALTHCARE, POST-ACUTE CLINICAL CARE, HOSPICE AND HOME INFUSION APPLICATIONS

FIELD OF INVENTION

The present invention generally relates to a system for generating, managing, accessing and storing documents and document data, and more particularly to an automated document information system which uses a phone as an optional or adjunct user interface for information input and output.

BACKGROUND OF THE INVENTION

There are many industries (e.g., home health care services, on-site maintenance and repair services, and the like) which require workers to travel to locations remote from a central office to carry out a particular task. For instance, the remote S locations could be locations around the state, county or city in which the central office site is located. Moreover, the remote location could merely be various locations around a large facility where the central office is located (e.g., rooms in a hospital, nursing home, factory, office complex, etc.). In many cases, there is a need to generate and/or receive information related to the task carried out at the remote location. The individual at the remote location (e.g., visiting nurse, home health aide, social worker, allied therapy professional, service technician, etc.) may need to access up-to-date or important information about a client (e.g., a patient or customer), or a device (e.g., an appliance), before beginning or completing a task. Moreover, the individual at the remote site may need to document tasks performed, test results, conditions observed, and other information pertinent to the task.

In the field of home health care, paper files have typically been used to record client information and document visits. Paper files have several serious drawbacks. In this regard, they are time consuming to generate, difficult to maintain, and easily corrupted. Moreover, they are often illegible, require the use of costly paper media, and are expensive and time consuming to duplicate.

While the use of a laptop computer or other handheld data entry device can reduce the reliance on paper documents, laptop computers and other handheld data entry devices pose their own problems when used in the field. Among these problems, they are costly to purchase and maintain. They also require the personnel in the field to have at least basic typing skills. Many people find typing more cumbersome and time consuming than handwriting. Laptop computers are also prone to theft and damage when used in the field. Furthermore, field personnel must be trained on the use of the computer and the associated software.

The present invention addresses the problems presented by both paper-based and entirely computer-based document information systems, as well as other drawbacks of the prior art.

SUMMARY OF THE INVENTION

According to the present invention there is provided a document information system for entering, retrieving and managing document information including both phone-based and computer-based user interfaces.

An advantage of the present invention is the provision of a document information system that allows for increased productivity and simplicity for tasks requiring data acquisition, document generation and information retrieval.

Another advantage of the present invention is the provision of a document information system that has simple, intuitive and friendly user interfaces.

Another advantage of the present invention is the provision of a document information system that has both phone-based and computer-based user interfaces.

Another advantage of the present invention is the provision of a document information system that generates accurate, complete and legible documents.

Another advantage of the present invention is the provision of a document information system that reduces the opportunity for entry of erroneous or fraudulent information.

Another advantage of the present invention is the provision of a document information system that does not require expensive equipment for use in the field.

A still further advantage of the present invention is the provision of a document information system that significantly reduces the reliance on paper-based documents.

A still further advantage of the present invention is the provision of a document information system that can be interfaced with billing, payroll, scheduling and other computer systems.

A still further advantage of the present invention is the provision of a document information system that allows for data entry solely through spoken words and keypad entries.

Still another advantage of the present invention is the provision of a document information system that allows for multi-lingual communications.

Still another advantage of the present invention is the provision of a document information system that allows the generation of complex documents using a phone as the primary data acquisition input device.

Still another advantage of the present invention is the provision of a document information system that allows previously stored document information to be retrieved and reviewed over a phone.

Still another advantage of the present invention is the provision of a document information system that generates customized data fields for associated computer system.

Still another advantage of the present invention is the provision of a document information system that verifies completion of events related to a task.

Still another advantage of the present invention is the provision of a document information system that verifies authorization for a user to complete a task.

Still another advantage of the present invention is the provision of a document information system that tracks supplies used to complete a task.

Yet another advantage of the present invention is the provision of a document information system that allows for a simple and efficient means for data entry, record keeping, and reporting.

Yet another advantage of the present invention is the provision of a document information system that integrates documentation with voice mail.

Yet another advantage of the present invention is the provision of a document information system that enables automated and efficient medical data documentation and record management.

Still other advantages of the invention will become apparent to those skilled in the art upon a reading and understanding of the following detailed description, accompanying drawings and appended claims.
}

BRIEF DESCRIPTION OF THE DRAWINGS

The invention may take physical form in certain parts and arrangements of parts, a preferred embodiment and method of which will be described in detail in this specification and illustrated in the accompanying drawings which form a part hereof and wherein:

FIGS. 4A–4D are flowcharts illustrating a series of basic operations of a phone driver;

FIGS. 13A–13D are exemplary calendar displays generated by the verification module;

FIGS. 15–40 illustrate an exemplary chart generated in accordance with the present invention.

DETAILED DESCRIPTION OF THE PREFERRED EMBODIMENT

While a preferred embodiment of the present invention will be described with particular reference to a document information system for use in connection with home healthcare, post-acute clinical care, hospice and home infusion applications, the present invention is also contemplated for use in other "field service" applications, such as on-site service for appliances and utilities. In this regard, the present invention finds utility in any application where data is generated and/or accessed by persons located at a remote site or at various locations within a large facility. Moreover, it should be appreciated that the term "document data" as used herein refers to any data acquired, processed, stored or retrieved via the document information system of the present invention.

Figure 1:
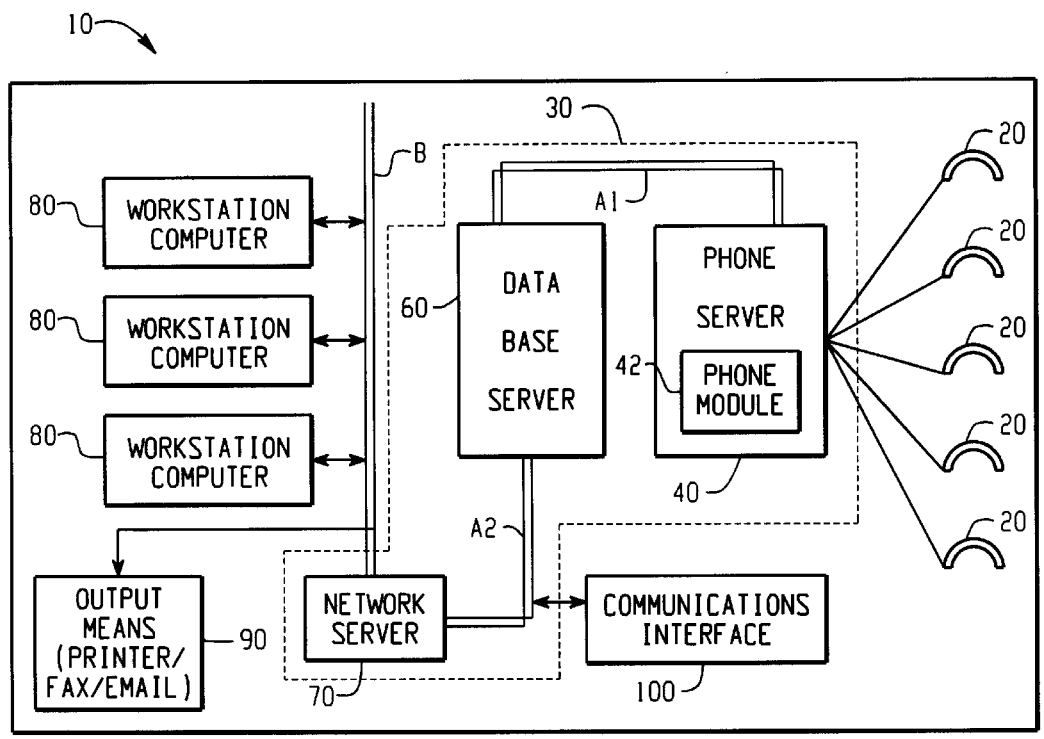
FIG. 1 is a block diagram of the basic hardware configuration for a document information system, according to a preferred embodiment of the present invention.

Referring now to the drawings wherein the showings are for the purposes of illustrating a preferred embodiment of the invention only and not for purposes of limiting same, FIG. 1 shows the basic hardware configuration of the document information system 10. Document information system 10 is generally comprised of a computer server system 30, one or more workstation computers 80, output means 90, and a communications interface 100.

In a preferred embodiment of the present invention, one or more phones 20 are linked to document information system 10 through a telephone system (public or private), or through any other voice communications system, including satellite, computer network (e.g., the Internet) and the like. Phones 20 are the primary interface device to document information system 10 for field users, and may take many forms including a standard telephone, a portable phone, cellular phone or Internet telephony device. Phones 20 are used, among other things, to verbally prompt the user, accept codified (e.g., numeric) input from a user via a phone keypad, and accept verbal responses from the user. A complete description of the operation of document information system 10 will be provided below.

Server system 30 is generally comprised of a phone server 40, a database server 60 and a network server 70. These servers can reside on a single computer system or may be suitably distributed among two or more computers systems. Accordingly, communication paths "A1" and "A2" may be within a single computer system, or between two computer systems connected via a computer network, such as a Local Area Network (LAN), on a Wide Area Network (WAN), or the Internet Furthermore, each of the servers 40, 60 and 70 may include one or more computer systems.

It should be appreciated that when phone server 40 is located at a different physical location than database server 60, a high-speed communications network may be used to link the servers. This allows for "local" phone calls to phone server 60, while still maintaining database server 60 at a central facility remote from phone server 40.

According to a preferred embodiment of the present invention, phone server 40 is a dedicated PC computer running Windows NT operating system. One or more voice cards (e.g., Dialogic or Dialogic-compatible) are installed in this computer. The primary function of the voice cards is to provide an electronic interface by converting digitized voice data to analog voice data, and vice versa Phone server 40 is basically responsible for such items as answering phone calls, collecting data entered by the user (i.e., voice data spoken into the phone and alphanumeric data entered through a phone keypad), storing received data in a database, and audibly presenting stored data to a user over the phone (i.e., outputting "spoken" data).

Database server 60 provides a database including a plurality of database files 62. In a preferred embodiment of the present invention, the database takes the form of a database program such as Microsoft Access or SQL. Database server 60 is basically responsible for optimizing requests to the database, queuing up the requests and maintaining database integrity and security.

In a preferred embodiment of the present invention, the database includes such tables as CLIENT INFORMATION (client's personal, physical, medical, and other health information), VISITS (information about client visits, e.g. date, time, mileage, etc.), EMPLOYEE (employee's personal, employment, specialty, access information, etc.), ACTIVITY LOG (activity information collected by what was done by phone and workstation), CLIENT INFORMATION FORM (information about the care plan, e.g., admission, discharge, medication, visit schedules, etc.), and 485/487 FORMS (information about the care plan, e.g., admission, discharge, medication, visit schedules, etc.).

According to a preferred embodiment of the present invention, the database include lookup tables such as PHYSICIAN (referral physician's name, office information, etc.), ADDRESS (states, cities, and zip codes), INSURER (insurance information), HOSPITAL (hospital information), NUTRITIONAL REQUIREMENT (client's nutritional requirements), MEDICATION (medication name, category, and instruction), LAB TEST (lab test date and results), DIAGNOSIS (primary, secondary, and surgical diagnosis), DME (durable medical equipment information), GOAL AND EXPECTED OUTCOMES, SKILLS AND TASKS, and MEDICAL SUPPLIES.

Furthermore, database server 60 stores digitized voice data, such as voice mail messages and narrative voice data, as will be explained below.

Network server 70 provides the communication between workstation computers 80 and database server 60 and (optionally) between phone server 40 and database server 60. It should be appreciated that there may be one or more network server computers 70 to enable the network communications.

Workstation computers 80 provide a computer-based interface to servers 30. These computers may be located in a central office, a branch office, or a remote location (e.g., a home). Workstation computers 80 are typically connected with servers 30 via a communications path B, but may also be linked via a modem, or other communications interface. It should be understood that path B is a primary communications path of document information system 10, and may include one or more of the following connection methods: Local Area Network (LAN), Wide Area Network(WAN), and the Internet.

Workstation computers 80 may serve one or more functions. In this regard, workstation computers 80 may be used to access and configure documents on database server 60, and provide a substitute user interface for phones 20. Where workstation computer 80 serves as a substitute user interface for phones 20, workstation computer may take the form of a portable laptop computer for convenient field use. A Graphical User Interface (GUI) module 82 provides a convenient user interface for carrying out the foregoing functions. GUI module 82 will be described in detail below. Workstation computers 80 may also provide a service interface to document information system 10 for technicians to service document information system 10, and serve as a computer system for billing and/or payroll (i.e., receiving data stored in database server 60).

It should be further appreciated that workstation 80 may also include a sound card for playback of audible voice data through a speaker. In this regard, verbal descriptions may be spoken over the phone by the user, and entered as audible voice data (e.g., voice mail messages or narrative) that is stored in a digitized form in database files 62. The audible voice data may be subsequently played back (e.g., like a cassette player), and manually transcribed into text data. In this regard, a transcriber plays back audible voice data like a cassette player, using a software interface, or mechanical foot pedal device to control the playback through a sound card, and transcribes the audible voice data into text data (e.g., human-readable narrative text or messages). Alternatively, the voice messages may be automatically converted to text data using well known conventional voice recognition technology. This eliminates the need for a sound card and a human transcriber.

Moreover, workstation 80 may also include an audio input means (e.g., a microphone) for directly inputting audible voice data for storage in database files 62. This provides an alternative means for entering audible voice data, other than phones 20. For instance, a workstation 80 could be used to record a voice mail message that is associated with a user, such that when the user is logged into document information system 10 they receive a "playback" of the voice mail message. If the voice mail message is associated with a client, then when information associated with that client is accessed, the previously stored voice mail message is replayed to the user.

Output means 90 provides a human-readable output (e.g., hard copy) of data stored in data base server 60. In this regard, output means 90 may take the form of one or more printers, fax machines, plotters, or other hard copy display devices. Furthermore, output means 90 could take the form of an electronic mail gateway.

Communications interface 100 provides yet another interface for accessing document information system 10. In a preferred embodiment, communications interface takes the form of a modem, which allows for a remote connection to document information system 10 for the purpose of technical support. In this regard, communications interface 100 provides a dedicated communications path for technical support personnel to provide diagnostics, database maintenance, system monitoring, software upgrades, and the like, from a remote location. However, it should be understood that communications interface 100 is also suitable for use in the same manner as communications path B (e.g, to connect a workstation computer).

The software modules of the present invention will now be described in detail. The present invention includes phone modules 42, GUI modules 82, interface modules 92 and utility modules 102 (FIG. 2B). Each of these modules communicates with database server 60.

Figure 2A:
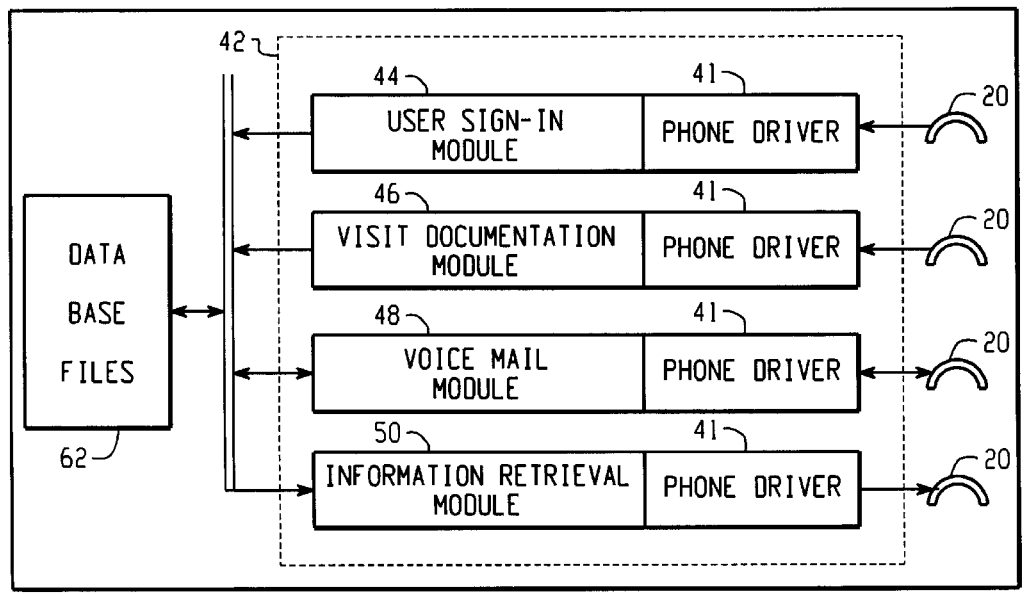
FIG. 2A is a block diagram illustrating the basic software configuration for interfacing phones with the document information system of the present invention.
Figure 2B:
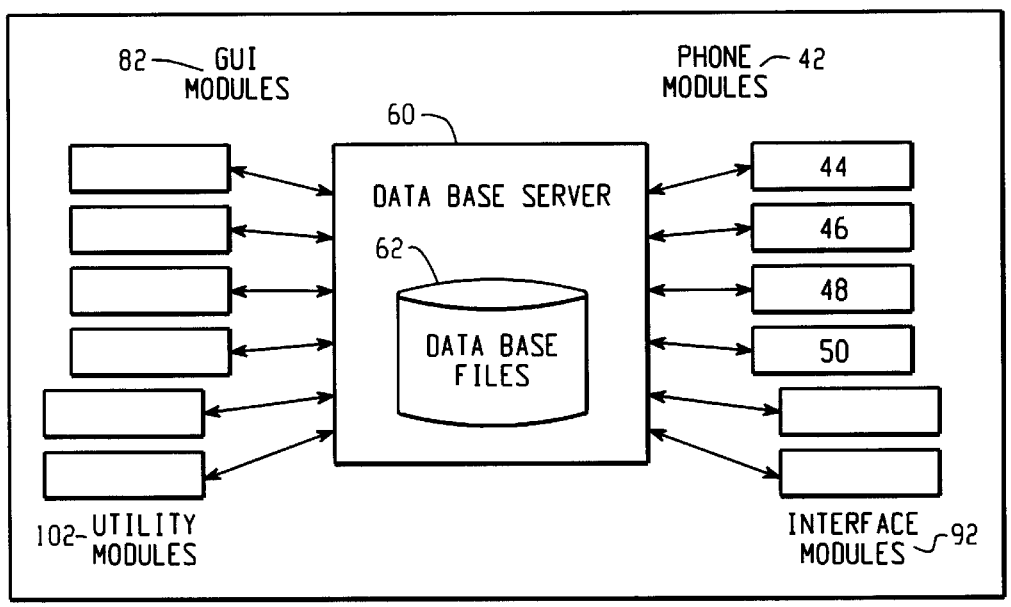
FIG. 2B is a block diagram illustrating the basic subsystems of the present invention.

Referring now to FIG. 2A, there is shown phone modules 42 running on phone server 40. A suitable software package, such as Visual Voice, may be used to build phone module 42. Phone module 42 provides a "voice user interface" (VUI) to document information system 10. Phone driver 41 is a software module that supports all of the phone interaction features, which are described below. There is one operational phone driver 41 for each active phone line. Each of the following modules utilize phone driver 41.

A main phone task module 200 (FIG. 5) provides the main logic stream for each phone call. It activates various basic function sub-modules (i.e., user sign-in module 44, visit documentation module 46, voice mail module 48 and information retrieval module 50). User sign-in module 44 accepts and verifies a user ID associated with a user. Each user ID is associated with a user "type." In this regard, a "type code" is stored in database server 60. The "type code" is used to control access limits and scope of interaction with document information system 10. In this regard, some information and some "modules" may not be accessible by all user "types." It should be noted that "type codes" may be user-defined. Moreover, the concept of "type" may be extended to other data items, such as the client In this regard, a "client-type" may be established and stored as part of a client's chart. Thus, the user's access limits and scope of interaction with documentation system 10 is keyed to the "client type". The chart may also include client identification information (e.g., a client id) for identifying the client that the chart is associated with.

Visit documentation module 46 allows a user to enter visit information including: visit times, physiological data, mileage, codes for tasks performed, supplies used, a detailed narrative (i.e., audible information), and other user-defined data items embedded in the narrative. Voice mail module 48 allows a user to retrieve and send voice mail messages. The messages may be "keyed" to a user ID and/or a chart ID, thus associating a message with a particular user or client. Information retrieval module 50 allows a user to retrieve information from the database residing on database server 60. This information may be in the form of alphanumeric or keyword phrases that are "spoken" by a computer (i.e., audible over the phone). This module can also trigger information to be sent to a remote location via such means as fax, Email, etc. A complete description of the foregoing modules is provided below.

It should be appreciated that the audible voice data discussed above (i.e., narrative and voice mail messages) are preferably digitized for storage in a digital medium.

Database server 60 allows multiple processes to simultaneously access database files stored therein. Moreover, database server 60 supports local and remote access to database files 62 with a variety of network schemes. In addition, database server 60 provides many data integrity checks and controls access to database files 62. Backup and recovery schemes are also supported.

Database server 60 stores files and tables, including those relating to: agency information, employee information, payor information, client (i.e., patient) information, task codes (summary of activities), visit data, treatment plan data, narrative voice files, voice mail files, and voice files for prompts supporting multiple languages.

Figure 3:
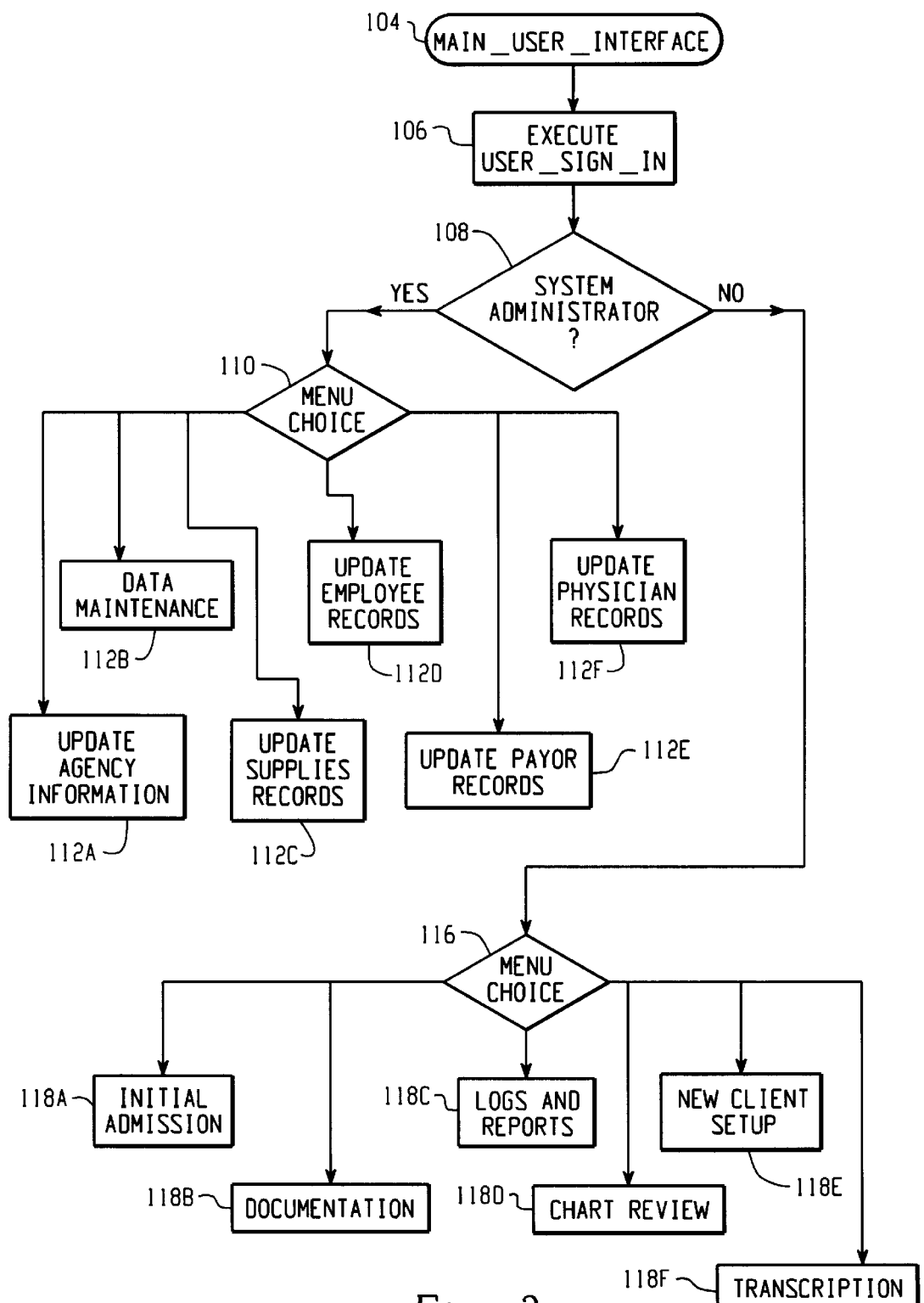
FIG. 3 is a flow chart illustrating operation of the GUI module.

GUI modules 82 run on workstation computers 80, and include several different types of modules. A main_user_interface 104 of GUI modules 82 will now be described with reference to FIG. 3. A user sign-in routine is executed to accept and verify a user ID (step 106). A user "type" code is associated with each user ID is retrieved for the database on database server 60. The "type" code is used to control access limits and scope of interaction with document information system 10. For instance, access to portions of document information system 10 may be limited to users having a "type" code for system administrators (step 108). If the user's "type" code is for system administrator then a first series of menu choices are made available to the user (step 110). The menu choices may include updating agency information (step 112A), data maintenance (step 112B), updating supplies records (step 112C), updating employee records (step 112D), updating payor records (step 112E) and updating physician records (step 112F).

As indicated above, the concept of "type" may be extended to other data items, such as the client. In this regard, a "client-type" may be established and stored as part of a client's chart. Thus, the user's access limits and scope of interaction with documentation system 10 is keyed to the "client type." The chart may also include client identification information (e.g., a client id) for identifying the client that the chart is associated with.

Updating agency information 112A includes such functions as updating the address of a health care provider. Data maintenance 112B includes such functions as purging old records. A table of available supplies is updated using updating supplies records (112C), employee and physician information are updated in 112D and 112F, respectively. Payor information is updated in 112E.

User's having other "type" codes may have access to other portions of document information system 10, and thus presented with a different set of menu choices (step 116). For instance, the menu choices may include initial admission (step 118A), documentation (step 118B), logs and reports (step 118C), chart review (step 118D), new client setup (step 118E) and transcription (step 118F). For initial admission, a chart ID associated with the client is established in step 118A, and basic client information is entered in step 118E.

Documentation 118B allows a visit to be documented in a manner similar to that used by the phone module, which is described in detail below. In this manner, a laptop computer can be used in the field to document a visit. Logs and reports 118C allows such activities as listing clients, generating billing and payroll reports, generating transaction logs, generating quality assurance reports, generating regulatory reports (such as OASIS), and generating verification reports that verify completion of tasks. Chart review 118D allows the user to retrieve and view information in a client's chart Transcription 118F allows transcription of any voice data files (i.e., narrative and voice mail) using manual (e.g., foot pedals) or automated means (e.g., voice recognition). The transcription capability also includes special coding for user-defined fields embedded in voice files, as will be described in further detail below.

One or more interface modules 92 are run on workstations 80 or database server 60. The interface modules are provided for communicating data between database server 60 and workstation 80, which may be running specialized accessory software, such as a billing and payroll program. In this regard, interface modules 92 may include a billing interface module for providing automatic data communication between database server 60 and a billing system computer workstation. As a result, user-defined fields which have been spoken and embedded in the transcription of the voice files can be detected and decoded for transferal to the billing system computer workstation. This function will be described in further detail below.

Furthermore, interface modules 92 are provided to transfer data between database server 60 and a remote computer system (e.g., a regulatory agency computer system) via communications path B or communications interface 100. A regulatory data transmission module supports collection and summary of data for periodic regulatory reports (such as OASIS). The interface module 92 provides the capability to automatically upload this data to an appropriate remote computer system (e.g., regulatory agencies).

A series of utility modules 102 integrated with communications interface 100, may be directly connected (via modem) with a remote technical support headquarters. A backup/restore module provides for automatic activation of a backup of database files 62 residing on database server 60. A database maintenance module provides periodic database maintenance which may be both automatic and semi-automatic. Features may include: monitoring of available database server space, compression, archive, consistency checks and fixes. A service module provides the capability to remotely access all aspects of server systems 30 from the remote technical support headquarters. This access can be initiated from document information system 10 or server system 30 can automatically initiate a message based on the detection of some abnormality. An invoicing module provides the capability for service invoices to be generated from a remote location.

Referring now to FIGS. 4A–4D, there is shown a series of flowcharts illustrating basic phone driver operations. The first operation is a New_phone_call operation 120 (FIG. 4A) which is used when establishing communication with system 10 via phones 20. System 10 answers the incoming phone call (step 122) and calls a get_menu subroutine for choosing a desired communication language (step 124). For example, system 10 may be configured to communicate with the user in French, Spanish or Russian. The get_menu subroutine will be described in detail below. The selected language is then enabled (step 126) and the main_phone_task routine is called (step 128) for this phone call. The main_phone_task routine will be described in detail below.

The get_menu subroutine 140 is illustrated by the flowchart shown in FIG. 4B. This subroutine allows the user to select a menu option. System 10 issues a prompt (step 142). It will be understood that the term "issue" as used herein refers to the activity wherein the system "speaks" over the phone to the user. In the present instance, the computer system may say: "Please select from one of the following three choices . . . ." The system then accepts an input response from a telephone keypad or a user-spoken response (step 144). Where a user-spoken response feature is employed, a simple voice recognition module is provided to interpret simple user responses such as "one," "two," "yes" or "cancel". The response is evaluated to determine if it is a valid response (step 146). If the response is invalid, then the system issues an invalid response message (step 148), e.g., the system "speaks" over the phone: "Your selection is invalid, please reenter . . . ." Once a valid response is received, a menu selection is returned (step 150).

A get_narrative subroutine 160 is illustrated by the flowchart shown in FIG. 4C. This subroutine is used by system 10 to record a narrative message input via a phone 20 (i.e., a voice response spoken by the user). The system issues a prompt (step 162) and begins accepting a voice response containing the narrative (step 166). After the narrative has been completed, the get_menu subroutine (described above) is called to query the user whether they want to review the narrative (step 166). If a review is requested the voice response is played backed over the phone (step 168). If no review is requested, then the get_menu subroutine is called to query the user whether they want to accept the narrative (step 170). If the narrative is not accepted then the subroutine returns to step 162. If the narrative is accepted, then the narrative will be stored in the database (step 172).

Figure 4D:
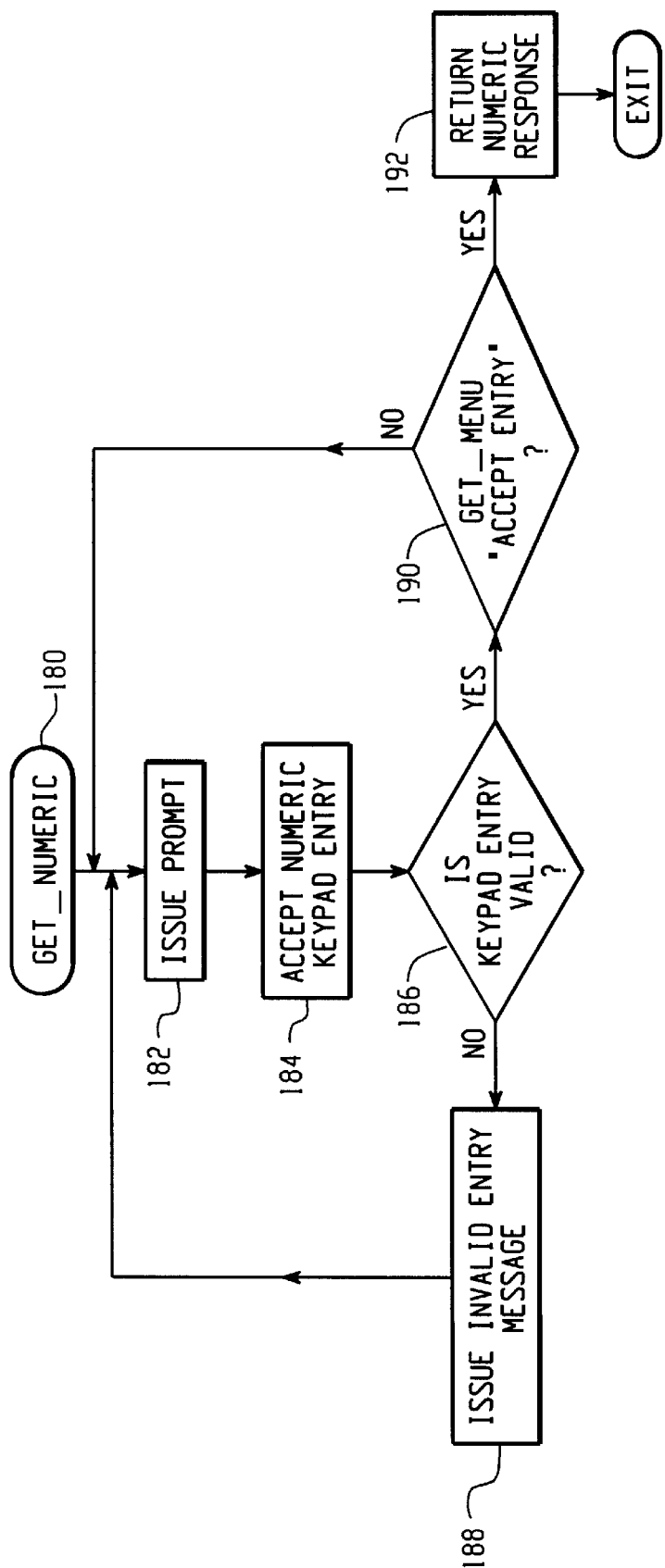

The get_numeric subroutine 180 is illustrated by the flowchart shown in FIG. 4D. This subroutine is used by system 10 to prompt a user for a numeric (or alphanumeric) input and to record the numeric input. The system issues a prompt (step 182) and begins accepting a numeric keypad entry from the phone keypad or a user-spoken response. It is determined whether the keypad entry is valid (step 186). If the entry is not valid, then an invalid entry message is issued (step 188) and the subroutine returns to step 182. If the entry is valid, then the get_menu subroutine is called to query the user whether to accept the entry (step 190). If the entry is not accepted, then the subroutine returns to step 182. If the entry is accepted then the numeric response is returned (step 192).

Figure 5:
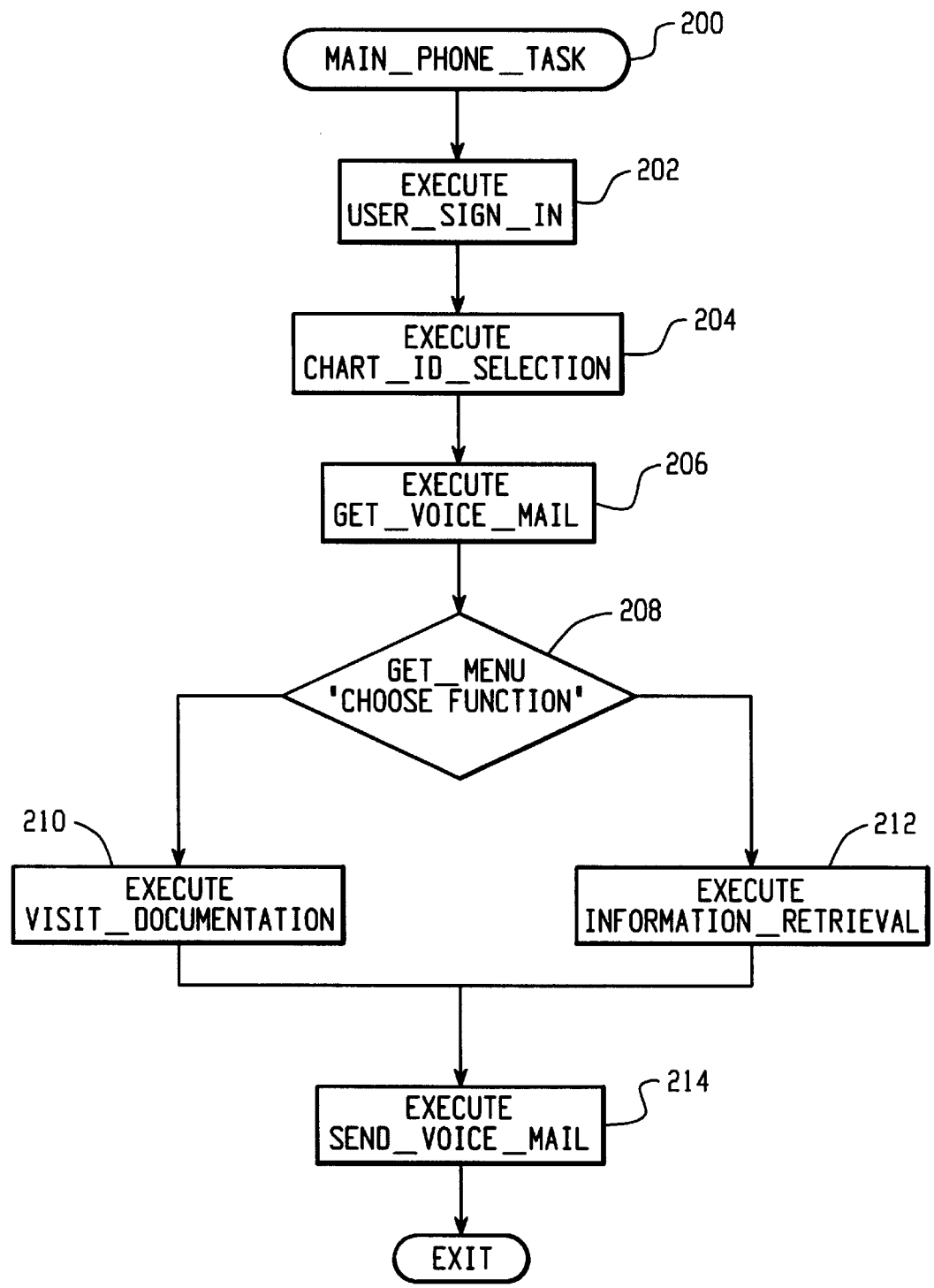
FIG. 5 is a flowchart illustrating a phone task procedure.

The flowchart of FIG. 5 provides an overview of the basic operations for the main_phone_task routine 200. This routine provides a format for communications between document information system 10 and phones 20. However, it will be appreciated that routine 200 as shown in FIG. 5 is provided solely for the purpose of illustrating a preferred embodiment of the present invention, and that routine 200 may take other suitable forms. In the embodiment shown in FIG. 5, a user_sign_in routine is executed (step 202), where the user signs-in (i.e., enters a "user id") to document information system 10 over phone 20. In this regard, the user identifies themself to document information system 10. Next, a chart_id_selection routine (step 204) is executed. In this routine, the user identifies a chart (i.e., enters a "chart id") corresponding to a client being treated. Thereafter, a get_voice_mail routine is executed (step 206), where voice mail associated with a "user id" and/or "chart id" is retrieved. Next, the get_menu subroutine is called to query the user as to a desired function (step 208). Among the available functions are a visit documentation routine (step 210) and an information retrieval routine (step 212). The visit documentation routine allows a user to document a visit with a client. The information retrieval routine allows a user to retrieve information stored in database files 62. Next, a send_voice_mail routine is executed (step 214), which allows a user to record voice mail. Each of the foregoing routines of the main_phone_task routine will be described in detail below.

Figure 6:
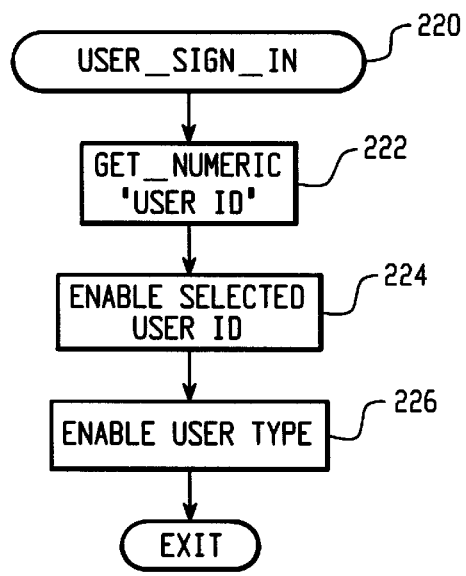
FIG. 6 is a flowchart illustrating a sign-in procedure.

FIG. 6 is a flowchart illustrating user_sign_in routine 220. Each user has an associated user id and user type. By entering the appropriate user id, a user can access information associated with the user id and user type corresponding to the user id. The get_numeric subroutine is called to prompt the user to enter a "user id" (step 222). The selected user id and user type are then enabled (steps 224 and 226), thus allowing access to associated information.

Figure 7:
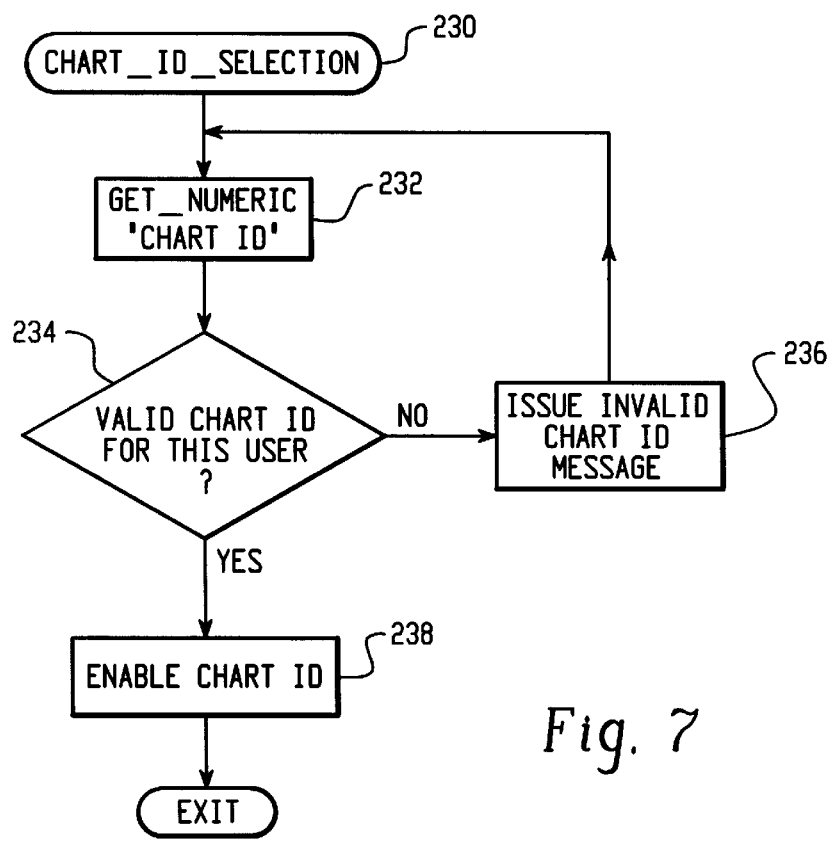
FIG. 7 is a flowchart illustrating a chart selection procedure.

FIG. 7 is a flowchart illustrating chart_id_selection routine 230. The get_numeric subroutine is called to prompt the user to enter a "chart id" (step 232). Next, it is determined whether the entered "chart id" is valid for this user (step 234). In this regard, it is determined whether the user having the specified "user id" and "user type" is allowed to have access to the chart associated with the "chart id." If the "chart id" is not valid, then an invalid chart id message is issued (step 236), and the routine returns to step 232. If the "chart id" is valid then the "chart id" is enabled (step 238), thus allowing access to the chart associated with the "chart id."

Figure 8:
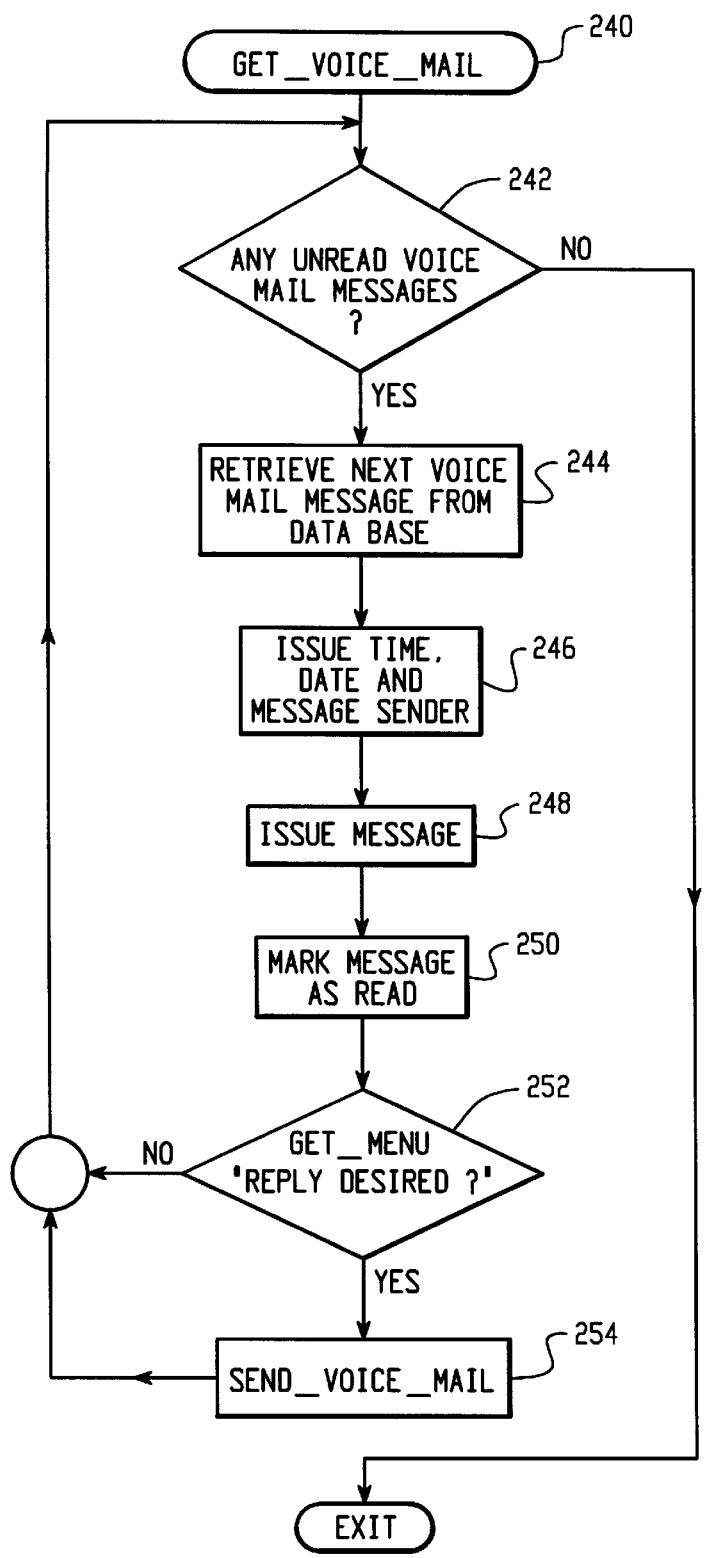
FIG. 8 is a flowchart illustrating a voice mail retrieval procedure.

FIG. 8 provides a flowchart illustrating the get_voice_mail routine 240. First, it is determined whether there are any unread voice mail messages (step 242). If their are no unread messages, then the routine is completed. If there are messages that have not been read, then the voice mail message is retrieved from database files 62 (step 244). Next, the time, date and message sender of the retrieved voice mail message is issued, i.e., spoken over the phone (step 246). Following this step, the retrieved voice mail message is issued over the phone (step 248). Thereafter, the retrieved message is marked as "read" (step 250). The get_menu subroutine is called to determine if a reply is desired (step 252). If no reply is desired, the routine returns to step 242 to determine if there are any additional unread voice mail messages. If a reply is desired, a send_voice_mail routine is called (step 254). Thereafter, the routine returns to step 242. It will be appreciated that in addition to a "reply desired?" query, the user may also be queried as to other well known voice mail options, such as replay, forward, delete, save, etc.

Figure 9:
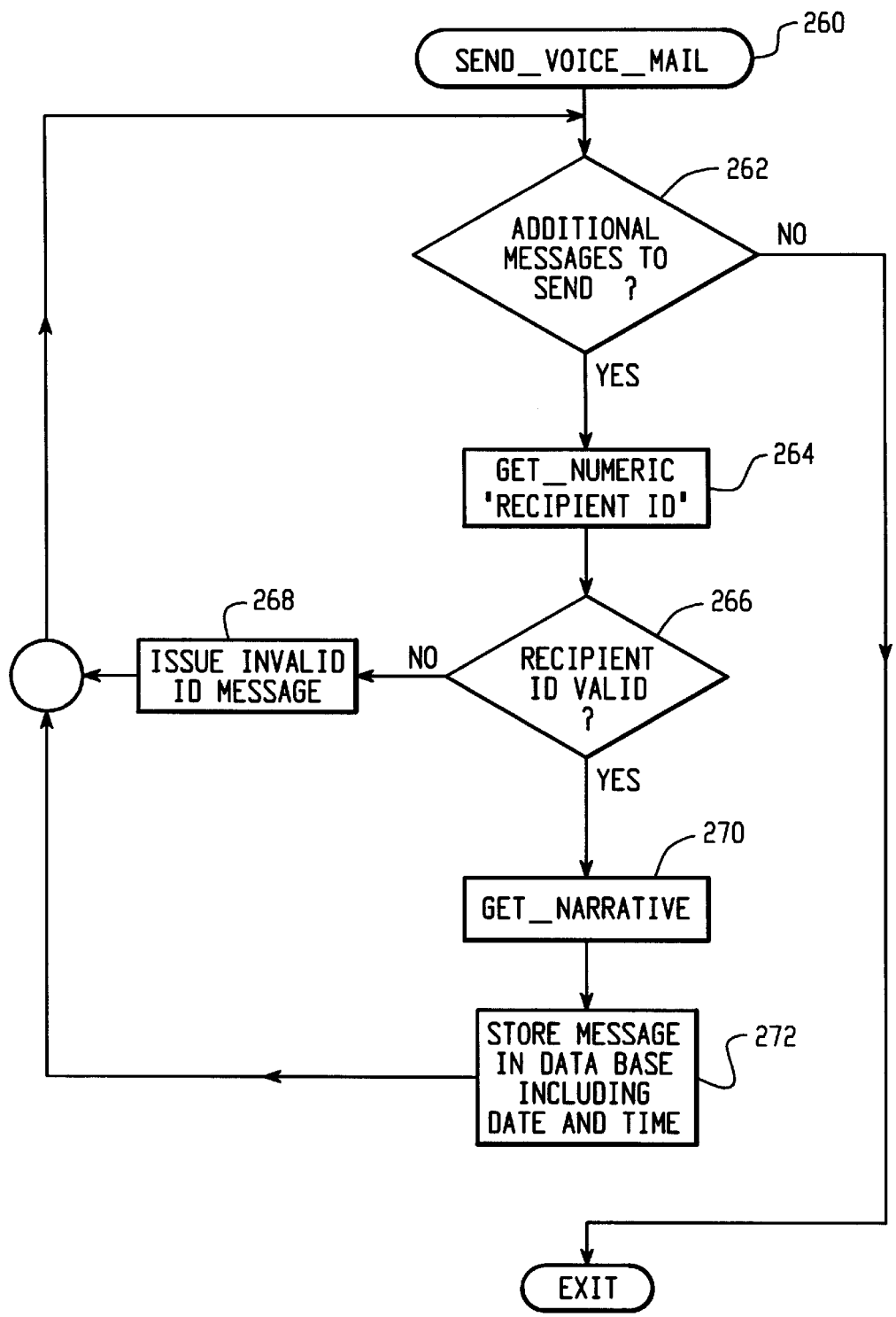
FIG. 9 is a flowchart illustrating a voice mail sending procedure.

FIG. 9 illustrates a flowchart for a send_voice mail routine 260. First, it is determined whether the user has any voice mail messages to send (step 262). If there are no messages to send the routine is completed. If a voice mail message is to be sent, then the get_numeric subroutine is called for entry of a "recipient id" (step 264). It is determined if the "recipient id" is valid (step 266). If the "recipient id" is not valid, then an invalid id message is issued over the phone (step 268), and the routine returns to step 262. If the "recipient id" is valid, then the get_narrative subroutine is called (step 270) to allow the user to record a voice mail message. The message is stored in the database files, including the date and time of the message (step 272). The routine then returns to step 262 to determine if any additional voice mail messages are to be sent.

Figure 10:
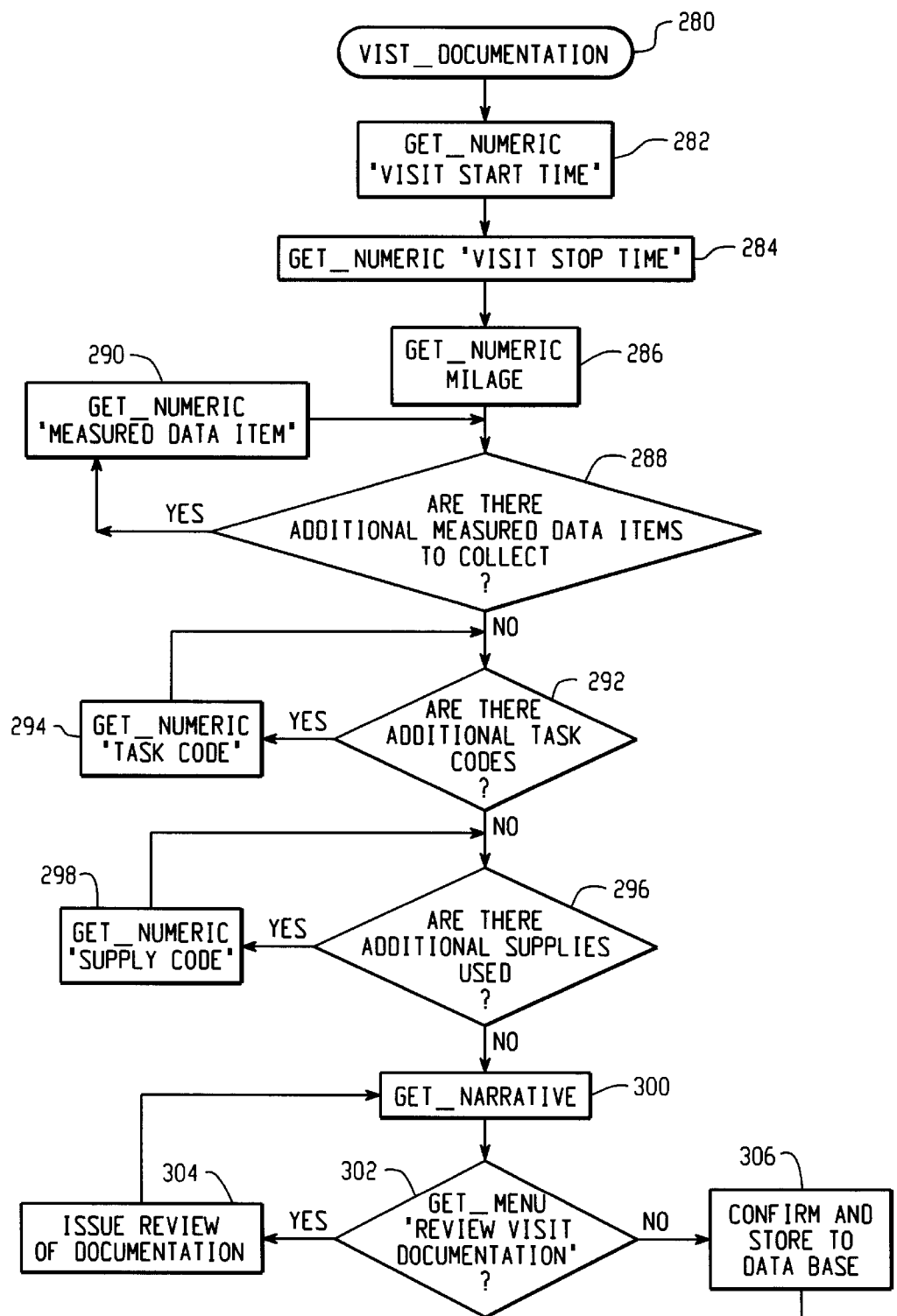
FIG. 10 is a flowchart illustrating a visit documentation procedure.

Referring now to FIG. 10, there is shown a flowchart for visit_documentation routine 280. This is the main routine for recording information regarding a "visit." The get_numeric subroutine is called in succession to allow the user to enter a visit start time (step 282), to enter a visit stop time (step 284), and to enter travel mileage to the client's location (step 286). Next, it is determined whether there are any "measured" data items to collect (step 288). "Measured" data items are such items that require the user to take a measurement of some physiological parameter (e.g., blood pressure, temperature, heart rate, etc.). The measured data items are stored in a table. The user is prompted to enter data for measured data items indicated in the table as being "required." If a measured data item is to be collected, the get_numeric subroutine is called to enter the measured data item (step 290). The routine then returns to step 288 to determine if any additional measured data items are to be collected. Once all of the measured data items have been collected, it is determined whether there are any task codes to be entered. The task codes are codes associated with the completion of different types of tasks (e.g., wound care, IV therapy, bath, feeding, etc.). If task codes need to be entered, then the get_numeric subroutine is called (step 294) for entry of the codes, and the routine returns to step 292. Once all of the task codes have been entered, it is determined whether any supplies were used during the visit to complete a task (step 296). If supplies were used, the get_numeric subroutine is called to enter a supply code (step 298) to identify a supply item. The routine then returns to step 296 to determine if any additional supply codes are to be entered. If no further supplies were used, get_narrative subroutine is called (step 300) to allow the user to leave a narrative message concerning the "visit." This narrative message may include such information as the condition of the client, the demeanor of the client, family problems, need for additional services, or other information relevant to treatment of the client. Thereafter, the get_menu subroutine is called to query the user whether they want to review all of the visit documentation that has been entered (step 302). If a user wants to review the visit documentation, then the system issues (i.e., "speaks") the documentation over the phone (step 304), and the routine returns to step 302. If a user does not want to review the visit documentation, then the user confirms that the visit documentation is to be stored to database files 62 (step 306).

Figure 11:
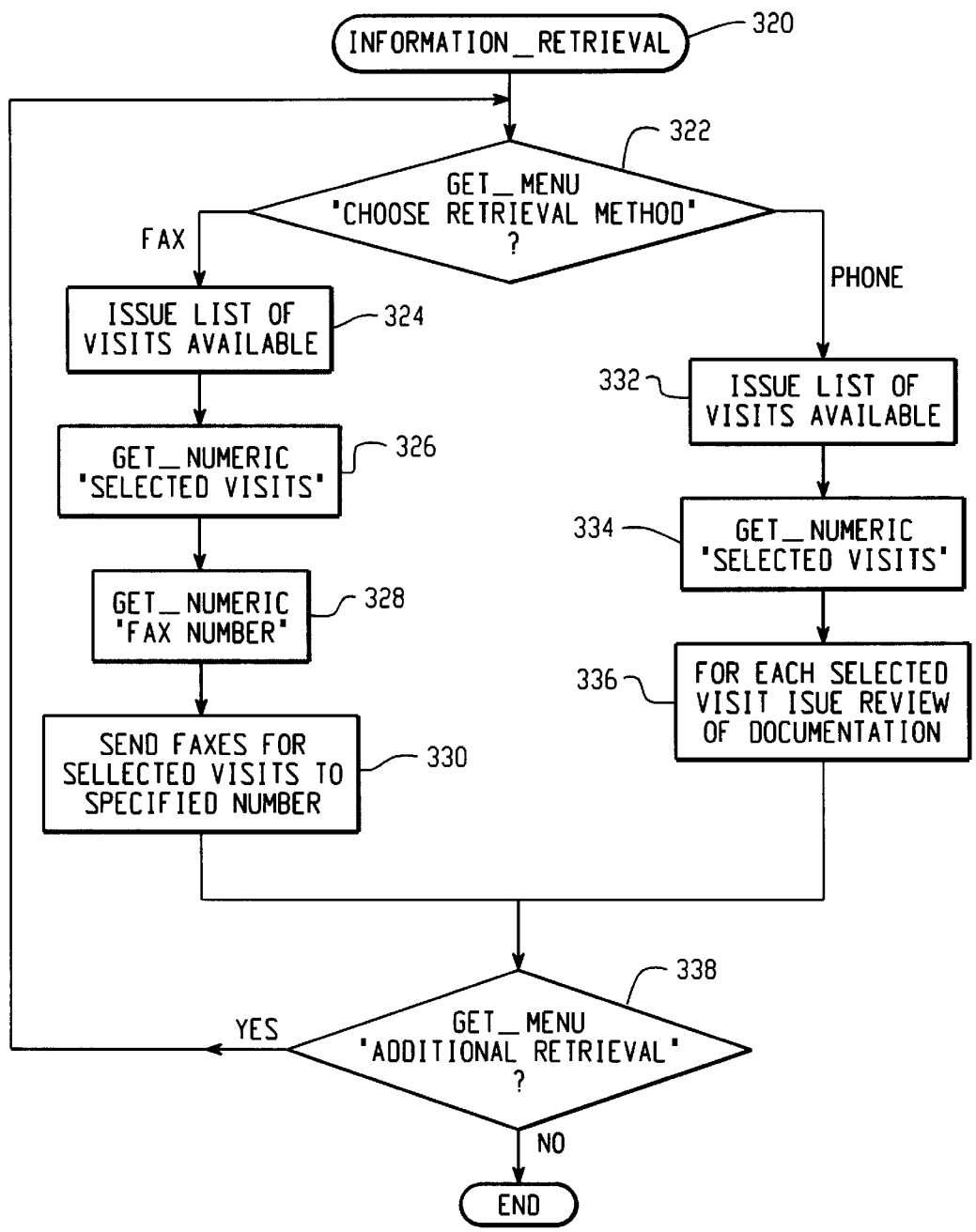
FIG. 11 is a flowchart illustrating an information retrieval procedure.

FIG. 11 is a flowchart illustrating information_retrieval routine 320. This routine allows a user to retrieve visit documentation which has been stored in database files 62. The get_menu subroutine is called to allow the user to choose a retrieval method (step 322). If the user selects "fax" retrieval steps 324–330 are executed. In particular, a list of available visits is "spoken" to the user (step 324), and the get_numeric subroutine is called to allow the user to enter the selected visits (step 326). Next, the get_numeric subroutine is called to allow the user to enter a fax number where the information will be faxed (step 328). Faxes are then sent to the specified number for the selected visits (step 330). Thereafter, the routine continues to step 338, where the get_menu subroutine is called to determine if the user desires to retrieve any additional information. If so, the routine returns to step 322. If no additional information is desired, the routine is completed.

In the case where a phone retrieval is selected at step 322, steps 332–336 are executed. In particular, a list of available visits is "spoken" to the user (step 332), and the get_numeric subroutine is called to allow the user to enter the selected visits (step 334). Documentation information for the selected visit is then "spoken" to the user over the phone (step 336). Thereafter, the routine continues to step 338, where the get_menu subroutine is called to determine if the user desires to retrieve any additional information.

As indicated above, GUI module 82 includes a verifier, which allows quick and simple verification that visits are taking place according to a predetermined plan. In this regard, the verifier provides a convenient, easily visualized, color coded, concise comparison of a "plan of treatment" with the actual visits performed and a summary of discrepancies.

Figure 12:
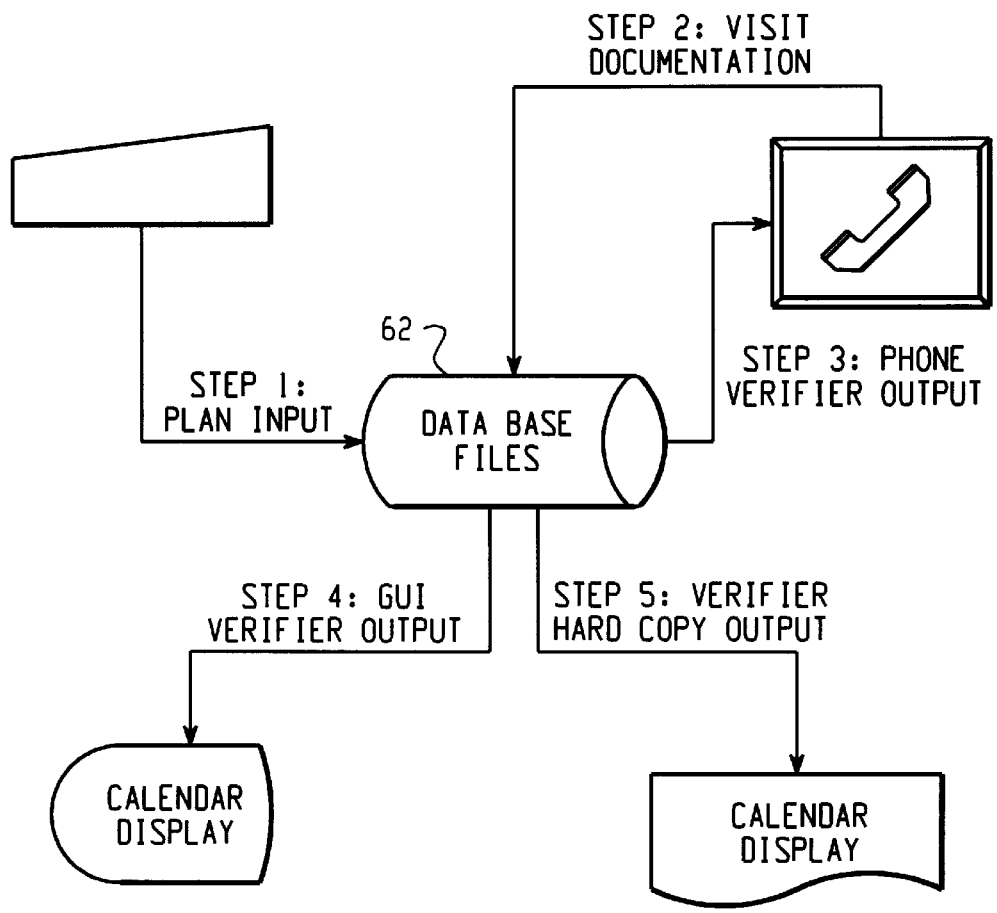
FIG. 12 is a flow diagram illustrating operations of a verification module.

Referring now to FIG. 12, there is shown a data flow diagram for use of the verifier of GUI module 82. First, a plan (e.g., a treatment plan) is entered into database files 62 (step 1). Next, visit documentation is generated using a phone (step 2). This involves the process of documenting a visit, as discussed above. A "phone verifier" (step 3) is used to determine if the user is authorized to complete a task. For instance, document information system 10 determines whether a due date has passed for completing a task, or whether the total number of authorized visits has been exceeded by a user of a particular discipline type. If no authorization is given, document information system 10 may be programmed not to accept visit documentation, or to trigger an authorization request from an appropriate authority. For instance the authorization request may be for additional visits by a particular type of home health care professional. A verifier output is generated on a workstation monitor (step 4). Alternatively, a hard copy output is generated (step 5). The verifier output of steps 4 and 5 is generated by the verifier of GUI module 82. A description of a preferred format for the verifier output will be described in detail below.

According to a preferred embodiment of the present invention, the verifier of GUI module 82 displays a visit pattern information in the form of four calendars: (1) What Should Occur Calendar, which shows the visits that are planned; (2) What Actually Happened Calendar, which is automatically generated based on the visits that were performed; (3) Verifier Calendar, which displays a summary of comparisons of the What Should Occur and What Actually Happened Calendars; and (4) The Ultimate Auditor Calendar, which combines the Verifier Calendar with a summary of what was documented throughout the chart.

Exemplary formats for the four verifier calendars are respectively shown in FIGS. 13A–13D. With reference to FIG. 13A, an exemplary What Should Occur Calendar includes the following information (in a first color): (a) Date; (b) Who—discipline (RN, HHA ,etc.); (c) When—the visit time and hours (if required) for all the disciplines; (d) Total hours/visits of what should occur at the end of a week on a discipline basis; and (e) Week number.

With reference to FIG. 13B, an exemplary What Actually Happened Calendar includes the following information (in a second color): (a) Date; (b) Who—discipline (RN, HHA ,etc.); (c) When—the visit time and hours (if required) have been completed for all the disciplines; (d) Total hours/visits of what was happened at the end of the week on a discipline basis; and (e) Week number.

Referring now to FIG. 13C, there is shown an exemplary Verifier Calendar, which includes the following information (in the first color, the second color or a third color): (a) Date (in the third color); (b) discipline (RN, HHA, etc.) and their visit hours; (c) Total hours/visits of both What Should Occur and What Actually Happened at the end of the week, on a discipline basis; and (d) Week number. With regard to display of the discipline/visits/visit hours, if the What Should Occur and the What Actually Happened match when compared, then the discipline and hours are displayed in the third color. If a visit is planned, but not performed, the visit hours are displayed in the first color. If a visit is planned but performed at a different time, then both the planned visit (displayed in the first color) and the performed visit (displayed in the second color) are shown. With regard to display of the total hours/visits, if the total hours/visits for What Should Occur and What Actually Happened match, then the total hours/visits in both Plan and Done are displayed in the third color. If not, the total in the "plan" column are displayed in the first color, and the total in the "done" column are displayed in the second color.

With reference to FIG. 13D, there is shown an exemplary Ultimate Auditor Calendar. The Ultimate Auditor calendar provide verification results for such items as: intake, discharge per discipline; discharge summary (DS), start of care (SOC), form 485, Dr. Orders (DO) Initial Assessment per discipline, history and physicals per discipline, home safety assessment per discipline, verifier calendar, supervisory visits (SV), home health aide—care plan (HHA CP), home health aide—care plan update (HHA CPU), case comments (CC), case summary (CS), case manager note (CMN), incident reports (IR), Meds/Labs. Dates associated with the foregoing information is readily apparent from the Ultimate Auditor Calendar.

It will be appreciated that the specific data items described above are for illustration purposes only, and that other data items may appear in the calendar displays of FIGS. 13A–13D. Moreover, the use of display attributes other than color may also be used in the foregoing calendar displays.

As indicated above, document information system 10 can generate narrative voice files. These narrative voice files may include "custom" data that is not part of a standard pre-defined document. Accordingly, document information system 10 is configured to encode the "custom" data so that it can be recognized and inserted into a custom data field of a customized document. The customized document is typically a document generated by a billing/payroll computer system, or other computer system linked to document information system 10.

Figure 14:
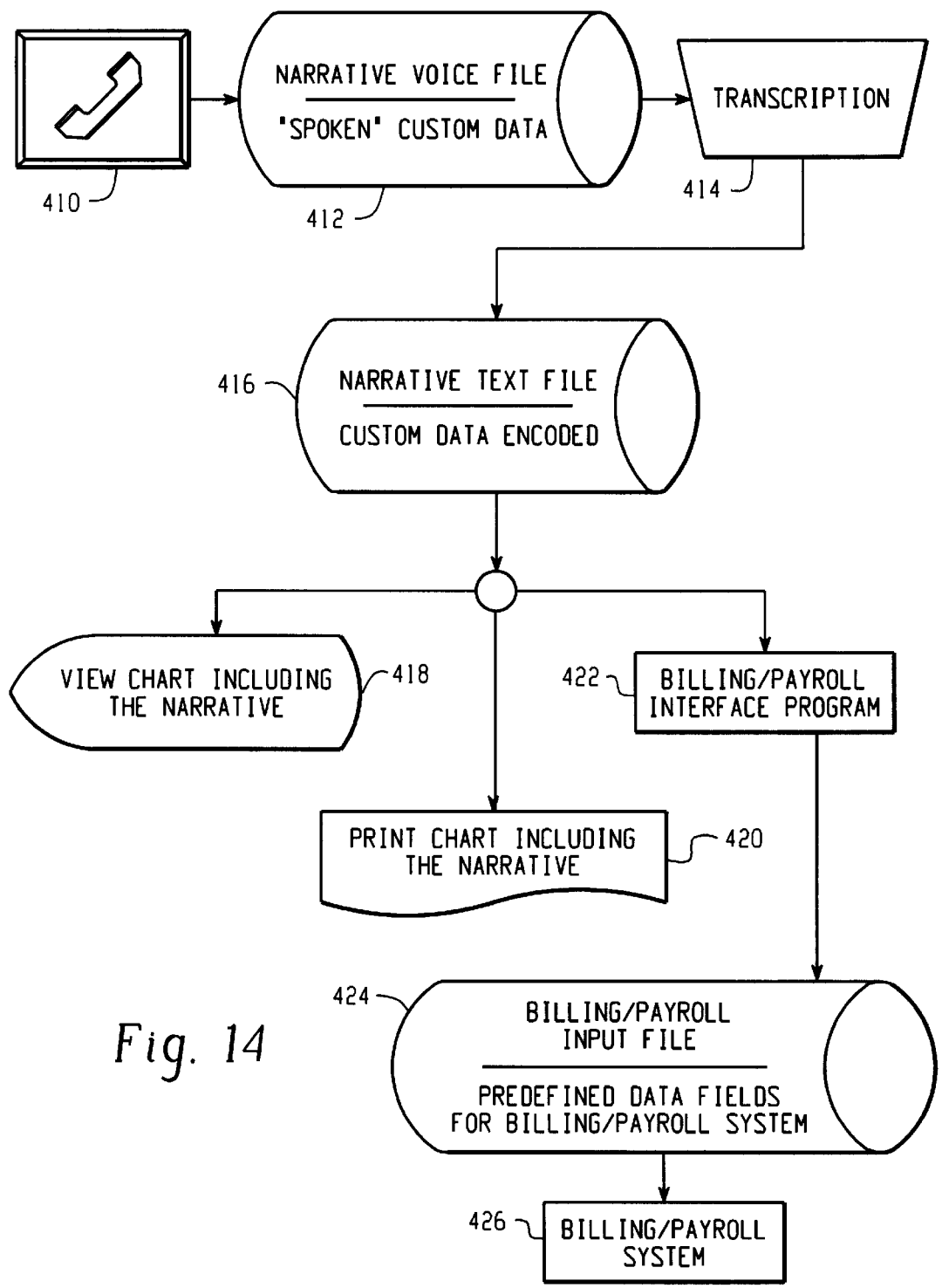
FIG. 14 is a flow diagram illustrating the flow of narrative data.

The process for accepting, encoding and decoding "custom" data will now be described with reference to FIG. 14, which shows a data flow diagram for narrative data. A user speaks into a phone (step 410) to record narrative voice data, which may include "custom" data associated with custom data fields. A narrative voice file is created to store the narrative voice data (step 412). During a transcription process (step 414), which may be manual or automatic, the narrative voice data is converted to narrative text data and stored in a narrative text file (step 416). During transcription, text corresponding to the narrative voice data is generated. When "custom" data is encountered, it is encoded. For example, a user may speak into the phone: "Mr. Smith refused to take a shower this morning. Client slept for about one hour this afternoon Company car. Two Miles." When the first two sentences are encountered during transcription, they are stored as standard narrative text data. The second two sentences are recognized as "custom" data or keywords. Therefore, when they are encountered the narrative text may be encoded with encoding symbols. For example, each item of "custom" data may be surrounded by brackets such as: [company car] [two miles]. As a result, the narrative text file now include unencoded standard narrative text data and encoded custom data. Alternatively, documentation system 10 may be programmed to parse narrative text for specifically identified custom data or keywords. In this case, no encoding (e.g., brackets) is needed.

Once the narrative text file has been generated several options are available. First, the contents of the narrative text file may be displayed on the monitor of a workstation, as part of a chart (step 418). The narrative text file may also be output to an output means, as part of a chart (step 420). Another option is to output the narrative text file to an interface program (e.g., a billing/payroll interface program), wherein the narrative text file is scanned for encoded custom data (step 422). An interface program decodes the custom data fields and translates them into a form needed by another computer system. In this regard, the interface program looks for the encoding symbols (e.g., brackets), and/or directly for the custom data or keywords, where no encoding is used. During this "decoding" process, the custom data is extracted from the narrative text file and output to an input file (step 424). The input file includes predefined data fields that are recognized by another computer system, such as a billing/payroll system. The custom data is inserted into the appropriate predefined data fields. Alternatively, appropriate data associated with the custom data is inserted into the appropriate predefined data fields. Other data generated by document information system 10 is also appropriately inserted into predefined data fields. The data stored in the predefined data fields in then output to another computer system, such as a billing/payroll system (step 426).

FIGS. 15–40 illustrate a complete chart as generated by document information system 10. More specifically, FIGS. 15A–15B show an exemplary client information report, FIG. 16 show an exemplary history and physical report, FIGS. 17A–17C show exemplary 485 forms, FIGS. 18A–18B show exemplary 487 forms, FIG. 19 shows exemplary doctor's orders report, FIGS. 20A–20B show an exemplary visits report, FIG. 21 shows exemplary medications report, FIG. 22 shows exemplary lab tests & results report, FIG. 23 shows exemplary case comments report, FIGS. 24A–24D shows an exemplary home health aide (HHA) plan, FIG. 25 shows exemplary supervisory visits report, FIGS. 26A–26B shows an exemplary history and physical report from a physical therapist (PT), FIGS. 27A–27C shows an exemplary history and physical report from an occupational therapist (OT), FIGS. 28A–28B shows an exemplary history and physical report from an SLP, FIG. 29 shows an exemplary history and physical report from a social worker (SW), FIG. 30 shows an exemplary home safety assessment report, FIG. 31 shows an exemplary incidents and occurrences report, FIG. 32 shows an exemplary case summary report, FIG. 33 shows exemplary case manager's comments, FIG. 34 shows an exemplary discharge summary, FIG. 35 shows an exemplary audit page, FIG. 36 shows an exemplary outcome data report, FIG. 37 shows an exemplary calendar report, FIG. 38 shows an exemplary visit report, FIG. 39 shows exemplary phone instructions, and FIG. 40 shows an exemplary billing report.

The invention has been described with reference to a preferred embodiment. Obviously, modifications and alterations will occur to others upon a reading and understanding of this specification. As indicated above, the present invention is not limited solely for use in connection with the home health care industry, but finds application in any industry in which documentation is generated and retrieved from a remote location. For instance, in the case of the appliance service industry, the present invention could be used in connection with data such as customer identifiers, service personnel identifiers, product model numbers, part numbers, warranty information, type of repair, repair dates, repair times, etc. Moreover, it should be appreciated that phone keypad data entry may be replaced with a voice recognition system to allow a user to enter data and respond to prompts using verbal commands. It is intended that all such modifications and alterations be included insofar as they come within the scope of the appended claims or the equivalents thereof.

Having thus described the invention, it is now claimed:

1. A document information system for use in the field of home healthcare, post-acute clinical care, hospice and home infusion, comprising:

storage means for storing document data, said document data including medical-related task information;

phone interface means for communicating said document data between said storage means and at least one associated phone, wherein the associated phone is used to input document data into the storage means, and retrieve said document data from the storage means and wherein said document data is inputted or retrieved from a user by audible voice data, alphanumeric data or combinations thereof;

computer interface means for communicating said document data between said storage means and at least one associated computer, wherein the associated computer is used to input said document data into the storage means, and retrieve said document data from the storage means; and verification means for verifying said medical-related task information wherein said verification means access to said storage means to generate one or more verification calendars, said verification calendars indicating dates associated with said medical-related tasks.

2. A document information system according to claim 1, including the step of a second verification means for verifying, whether a user is authorized to complete a medical-related task.

3. A document information system according to claim 1, wherein said verification means verifies the completion of one or more medical-related tasks.

4. A document information system according to claim 1, wherein a first verification calendar displays a first information set with a first attribute, a second verification calendar displays a second information set with a second attribute, a third verification calendar displays a third information set with a third attribute, said third information set derived from a comparison of said first information set to said second information set.

5. A document information system for use in the field of home healthcare, post-acute clinical care, hospice and home infusion, comprising:

storage means for storing document data, said document data including medical-related task information;

phone interface means for communicating said document data between said storage means and at least one associated phone, wherein the associated phone is used to input document data into the storage means, and retrieve said document data from the storage means; and wherein said document data is inputted or retrieved from a user by audible voice data, alphanumeric data or combinations thereof;

computer interface means for communicating said document data between said storage means and at least one associated computer, wherein the associated computer is used to input said document data into the storage means, and retrieve said document data from the storage means;

verification means for verifying said medical-related task information wherein said verification means access to said storage means to generate one or more verification calendars, said verification calendars indicating dates associated with said medical-related tasks, record generation means for generating a medical data chart including said medical-related task information.

6. A document information system according to claim 5, wherein said medical-related task information includes measured data associated with a client's condition, and task data associated with a medical-related task performed by a user.

7. A document information system according to claim 5, wherein said medical-related task information takes the form of both alphanumeric data and audible voice data.

8. A document information system according to claim 1, wherein said medical-related task information includes medical-supply data associated with supplies used to complete a medical-related task.

9. A computer-implemented method for generating medical-related documents, the method comprising:

audibly outputting information queries over a phone communications device for acquiring document data, said document data including medical-related task information;

receiving document data via the phone communications device in response to said information queries;

storing the received document data in a database means;

generating documents from the document data stored in said database means; and verifying said medical-related task information wherein said verifying means access to said verification calendar indicators dates associated with said medical related task information.

10. A method according to claim 9, wherein the step of verifying includes verifying whether a user is authorized to complete a medical-related task.

11. A method according to claim 10, wherein the step of verifying includes verifying the completion of one or more medical-related tasks.

12. A method according to claim 11, wherein the step of verifying includes generating one or more verification calendars, said calendars indicating dates associated with said medical-related tasks.

13. A method according to claim 12, wherein said calendars include a first verification calendar for displaying a first information set with a first attribute, a second verification calendar for displaying a second information set with a second attribute, and a third verification calendar for displaying a third information set with a third attribute, said third information set derived from a comparison of said first information set to said second information set.

14. A computer-implemented method for generating medical-related documents, the method comprising:

audibly outputting information queries over a phone communications device for acquiring document data, said document data including medical-related information;

receiving document data via the phone communications device in response to said information queries;

storing the received document data in a database means;

generating a medical data chart including said medical-related information verifying means access to said verification calendar indicators dates associated with said medical related task information.

15. A method according to claim 14, wherein said medical-related information includes measured data associated with a client's condition, and task data associated with a medical-related task performed by a user.

16. A method according to claim 14, wherein said medical-related information takes the form of both alphanumeric data and audible voice data.

17. A method according to claim 14, wherein said medical-related information includes medical supply data associated with supplies used to complete a medical-related task.

* * * * *